US005971951A

United States Patent [19]
Ruskewicz

[11] Patent Number: 5,971,951
[45] Date of Patent: Oct. 26, 1999

[54] AEROSOL EXTRUSION MECHANISM

[75] Inventor: Stephen J. Ruskewicz, Kensington, Calif.

[73] Assignee: Aradigm Corp., Hayward, Calif.

[21] Appl. No.: 09/162,262

[22] Filed: Sep. 28, 1998

Related U.S. Application Data

[63] Continuation of application No. 08/914,962, Aug. 20, 1997, Pat. No. 5,855,564.

[51] Int. Cl.$^6$ .................................................. A61M 11/00
[52] U.S. Cl. ........................................ 604/62; 128/200.14
[58] Field of Search ................................ 604/57–59, 62, 604/71, 131, 151, 152, 214, 191, 244, 61; 128/200.14, 200.17, 200.19, 200.23

[56] References Cited

U.S. PATENT DOCUMENTS

| | | |
|---|---|---|
| 3,259,077 | 7/1966 | Wiley et al. . |
| 3,669,104 | 6/1972 | Wyatt et al. ............................... 604/58 |
| 5,027,806 | 7/1991 | Zoltan et al. . |
| 5,037,396 | 8/1991 | Streeter .................................... 604/152 |
| 5,394,866 | 3/1995 | Ritson et al. . |
| 5,404,871 | 4/1995 | Goodman et al. . |
| 5,450,336 | 9/1995 | Rubsamen et al. . |
| 5,469,843 | 11/1995 | Hodson ..................................... 604/58 |
| 5,482,032 | 1/1996 | Smith et al. ............................... 604/58 |
| 5,509,404 | 4/1996 | Lloyd et al. . |
| 5,522,385 | 6/1996 | Lloyd et al. . |
| 5,558,085 | 9/1996 | Rubsamen et al. . |
| 5,608,647 | 3/1997 | Rubsamen et al. . |
| 5,647,349 | 7/1997 | Ohki et al. ................................ 604/58 |
| 5,694,920 | 12/1997 | Abrams et al. ...................... 128/200.16 |
| 5,743,250 | 4/1998 | Gonda et al. ....................... 128/200.22 |
| 5,769,070 | 6/1998 | Frati et al. .......................... 128/200.23 |
| 5,792,057 | 8/1998 | Rubsamen et al. ................. 128/200.14 |
| 5,813,397 | 9/1998 | Goodman et al. .................. 128/200.14 |
| 5,823,178 | 10/1998 | Lloyd et al. ....................... 128/200.14 |
| 5,829,435 | 11/1998 | Rubsamen et al. ................. 128/200.14 |
| 5,829,436 | 11/1998 | Rubsamen et al. ................. 128/200.14 |

FOREIGN PATENT DOCUMENTS

| | | |
|---|---|---|
| 0 358 002 | 3/1990 | European Pat. Off. . |
| 0 430 566 | 6/1991 | European Pat. Off. . |
| 2 673 142 | 8/1992 | France . |
| WO 96/09846 | 4/1996 | WIPO . |

*Primary Examiner*—Corrine McDermott
*Assistant Examiner*—Sharon Finkel
*Attorney, Agent, or Firm*—Renee A. Fitts; Bozicevic, Field & Francis LLP

[57] ABSTRACT

Devices for the generation of inhalable aerosols by extrusion through a porous membrane by a motor-driven cam assembly are disclosed. The device holds a drug formulation container in a drug release position. The package is comprised of a collapsible wall with an opening and a cover for the opening that includes a porous membrane having a plurality of pores therein with a diameter in the range of 0.5 to 6.0 microns. An electric motor in the device is powered by a battery to rotate a cam assembly having three cams. The first cam forces a clamping member (configured to correspond to the outer periphery of the container) against the periphery of the collapsible wall of the container, sealing the jointure of the collapsible wall to the cover of the container along the entire periphery, except for a small unsealed portion thereof. The second cam crushes the collapsible wall, forcing the contents of the container through the unsealed portion of the jointure. The third cam operates to move the empty container out of the drug release position, while moving a new container into position.

13 Claims, 10 Drawing Sheets

AEROSOL EXTRUSION MECHANISM

CROSS REFERENCES

This application is a continuation of earlier filed patent application Ser. No. 08/914,962, filed Aug. 20, 1997, now U.S. Pat. No. 5,855,564, issued Jan. 5, 1998, which application is incorporated herein by reference and to which application we claim priority under 35 U.S.C. §120.

FIELD OF THE INVENTION

This invention relates generally to the field of aerosolized drug delivery and specifically relates to mechanical devices which are used to deliver aerosolized formulations for patient inhalation.

BACKGROUND OF THE INVENTION

It has been known for some time that aerosolized formulations of drugs can be inhaled and absorbed through the lungs. The formulation can treat lung tissue topically and/or be absorbed into the circulatory system to have a systemic effect. In general, aerosolized particles must have a diameter of 12 microns or less. Topical lung treatment can be carried out using particles having a diameter in the range of 8.0 to 12.0 microns. However, these particles are generally too large to carry out affective systemic treatment which generally uses particles having a diameter in the range of 0.5 to 6.0 microns.

It is difficult to produce particles which are sufficiently small inhalation i.e., particles having a diameter of less than 12 microns. There are several different types of devices which allow for the production of these small particles. In one method referred to as a "dry powder inhaler" or DPI the particles are dispensed by means of bursts of large volumes of compressed air which entrain small amounts of the particulate to form a dust cloud or atomize some of a fluid to form a spray of fine droplets. However, this method results in losses of medicament and requires that the user have a source of large volumes of compressed air available. A more commonly used device is a "metered dose inhaler" or MDI which uses a low boiling point propellant in a pressurized canister. By releasing a valve on the canister a metered amount of formulation and propellant are released. The propellant "flashes" or quickly evaporates away leaving small particles of drug for inhalation. Although an MDI provides a self-contained and readily portable device to be constructed, the use of liquefied propellants is increasingly unacceptable from environmental and other grounds.

SUMMARY OF THE INVENTION

Devices and methods for the generation of inhalable aerosols by extrusion through a porous membrane are disclosed. The device holds a drug formulation package in a drug release position. The package is comprised of a collapsible wall portion which forms a container with an opening and a cover portion which includes a porous membrane having a plurality of pores therein with a diameter in the range of about 0.25 to about 6.0 microns. An electric motor in the device is connected to a power supply, preferably a battery, so as to rotate a cam assembly mechanically attached to the motor. The cam assembly contains up to three cams mounted on one or more camshafts, but preferably the cam assembly comprises three cams mounted on a single cam shaft with the cam positioned so as to form a single function.

Movement of the cam shaft rotates a first extrusion cam, so as to apply pressure to the container preferably in an amount of 50 bar or less, for example, 35 up to, but not including 50 bar, thereby collapsing the collapsible wall, and forcing the drug formulation from the package through the porous membrane. Preferably rotation of the extrusion cam actuates a reciprocating piston to apply the pressure to the package and crush the collapsible wall portion of the container.

Rotation of an optional clamping cam caused by movement of the cam shaft forces a clamping member (configured to correspond generally to the outer periphery of the container) against a planar portion of the device to seal all but a small portion of the periphery of the container against the cover while the extrusion cam applies pressure via the clamping member to the collapsible container wall, forcing the contents of the container out through the unsealed portion of the container's periphery and from there through the porous membrane.

An optional third advancement cam moves the package emptied by the operation of the extrusion cam out of the drug release position, and moves a new package into position. A new porous membrane is preferably used for each extrusion. However, it is possible to make more than one extrusion through the same membrane. The advancement cam is an eccentric cam operating in a dual axis space frame, and is fitted with a claw for engaging the emptied package and advancing a new package into the drug release position. In the preferred embodiment, the extrusion, clamping, and advancement cams are mounted on a single cam shaft thereby reducing mechanical components and coordinating the rotation and action of each cam relative to the others.

The motor is preferably actuated automatically by a signal received from a microprocessor which receives information from sensors regarding inspiratory flow and volume.

An object of the invention is to provide a breath actuated, motor driven device which generates an inhalable aerosol.

An advantage of the invention is that the formulation can be forced from the container using a pressure which is preferably always less than 50 bar, such as is provided by the extrusion cam.

Another advantage is that the cam assembly automatically removes the emptied package and moves a new package containing the formulation into position for administration of the next measured dosage.

A feature of the invention is that it is small and light weight (less than 0.5 kg.).

Another advantage is that an aerosol is created without the need for dry powders or propellants.

Yet another advantage of the invention is that an aerosol is created with a small amount of energy such as that which can be generated from batteries placed in a hand-held, portable device.

These and other objects, advantages and features will become apparent to those skilled in the art upon reading this disclosure with reference to the drawings as described below.

DETAILED DESCRIPTION OF THE PREFERRED EMBODIMENTS

Figure 1:
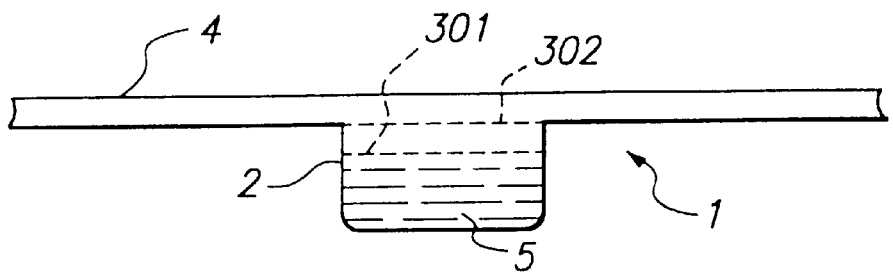
FIG. 1 is a cross-sectional view of a container used in carrying out the invention.

As used herein and in the appended claims, the singular forms "a," "an," and "the" include plural referents unless the context clearly dictates otherwise. Thus, for example, reference to "a formulation" includes mixtures of different formulations, reference to "an asthma attack" includes one or more of such events, and reference to "the method of treatment" includes reference to equivalent steps and methods known to those skilled in the art, and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference to describe and disclose specific information for which the reference was cited in connection with.

The publications discussed are provided solely for their disclosure prior to the filing date of the present application. Nothing herein is to be construed as an admission that the invention is not entitled to antedate such disclosure by virtue of prior invention. Publications dates shown are believed to be accurate but the actual date on which any disclosure becomes publicly available may later prove to be different.

DEFINITIONS

The terms "package" and "disposable package" are used interchangeably herein and mean a container or two or more containers linked together by an interconnecting means wherein each container preferably includes one or more channels which provide for fluid connection from the container to a porous membrane preferably not positioned directly over the container, and wherein each container includes at least one surface which is collapsible in a manner so as to allow the forced displacement of the contents of the container through a channel, a low resistance filter, and out of the porous membrane (without rupturing the container) in a manner such that the contents are aerosolized. The disposable package preferably includes one or more openings near the porous membrane through which air can be forced in a cassette or drug dispensing device described below. There are variations of the package, depending on factors such as whether the drug is stable when stored in a liquid form, or must be stored dry and combined with liquid immediately prior to aerosolization.

The contents of each container preferably comprise a formulation, preferably a liquid, flowable formulation which includes a pharmaceutically active drug and (if the drug is not liquid and of a sufficiently low viscosity to allow the drug to be aerosolized) an excipient carrier, i.e., preferably without any additional material such as preservatives which might affect the patient. Thus the formulation is a liquid with a relatively low viscosity that can be readily aerosolized, and preferably comprises a pharmaceutically active drug dissolved or dispersed in an excipient carrier. When the contents must be stored in a dry state, the package further includes another container that holds the liquid and can be combined with the dry drug immediately prior to administration.

The term "container" as used herein means a receptacle for holding and/or storing a drug formulation. The container can be single-dose or multi-dose, and/or disposable or refillable. Preferred containers are comprised of at least one collapsible wall and at least one opening which opening is in fluid connection with a porous membrane cover. The movable or collapsible wall is preferably designed so that the package can be collapsed by the application of a force in an amount of less than 50 bar. The porous membrane preferably includes a plurality of pores (10 or more) which are designed so that when the formulation is moved through the pores the formulation is aerosolized into particles which can be inhaled into the lungs. Accordingly, the pores generally have a pore size in the range of about 0.25 to about 6 microns.

The term "cassette" as used herein means a container which holds, in a protective cover, a container or a plurality of interconnected containers held in the cassette in an organized manner, e.g., interfolding or wound. The cassette is connectable to a dispensing device and preferably includes a power source, e.g., one or more batteries in the cassette which provide power to the dispensing device.

The term "porous membrane" as used herein means a membrane of material of any given shape, but preferably having a convex shape or flexible into a convex shape by the application of force, wherein the membrane has a plurality of pores with openings placed in a regular or irregular pattern, and which pores have a diameter in the range of 0.25 micron to 6 microns and a pore density in the range of $1\times10^4$ to about $1\times10^8$ a pores per square centimeter—10 to 10,000 pores per sq. mm. The pores may be planar with respect to the surface of the porous membrane material, or may have a conical or hour glass configuration. The membrane is preferably comprised of a material having a density in the range of 0.25 to 3.0 mg/cm², more preferably 1.7 mg/cm², and a thickness of about 2 to about 20 microns, more preferably 8 to 12 microns. The membrane material is preferably hydrophobic and includes materials such as polycarbonates and polyesters which may have the pores formed therein by any suitable method, including anisotropic etching through a thin film of metal or other suitable material. The membrane preferably has sufficient structural integrity to remain intact (without rupture) when subjected to force in an amount sufficient to force the formulation through the pores in about 1 second or less e.g., about 50 bar or less.

The term "low resistance filter" means a filter of material having any given shape, and having a plurality of pores placed in a regular or irregular pattern, and which pores have a diameter equal to or smaller than the pores of the membrane the filter having a porosity greater than that of the membrane. Preferably, the ratio of the porosity of the porous membrane to that of the low resistance filter is in the range of about 1:15 to about 1:100 or more; and the ratio of the diameter of the pores of the porous membrane to those the low resistance filter is in the range of from about 1:0.95 to 1:0.25. The flow resistance of the filter may be the same as, but is preferably substantially lower than, the flow resistance of the porous membrane used in conjunction with the filter. The filter is preferably comprised of a material having a density in the range of 0.25 to 3.0 mg/cm², more preferably 1.7 mg/cm², and a thickness of about 2 microns to about 20 microns, more preferably about 8 to 12 microns. The filter material is preferably hydrophobic and includes materials such as polycarbonates and polyesters which may have the pores formed therein by any suitable method, including anisotropic etching or by etching through a thin film of metal or other suitable material. The filter preferably has sufficient structural integrity such that it is maintained intact (i.e., will not rupture) when subjected to force up to about 50 bar during extrusion of the formulation through the pores.

The term "flow resistance" as used herein means the resistance associated with the passage of a liquid or aerosol through a porous material, e.g., through the porous membrane or the low resistance filter described herein. Flow resistance is affected by the size and density of pores in the porous material, the viscosity of a liquid passing through the material, and other factors well known in the art. The terms "low resistance" and "low flow resistance" are used interchangeably to mean a flow resistance half that or less and preferably one tenth that or less than the flow resistance of the porous membrane by having a porosity on the filter ten times that of the porous membrane.

The term "respiratory drug" as used herein means any pharmaceutically effective compound used in the treatment of any respiratory disease, particularly such diseases as asthma, bronchitis, emphysema and cystic fibrosis. Useful "respiratory drugs" include those which are listed within the Physician's Desk Reference (most recent edition). Such drugs include beta adrenergic agonists which include bronchodilators including albuterol, isoproterenol sulfate, metaproterenol sulfate, terbutaline sulfate, pirbuterol acetate, salmeterol xinotoate, formotorol; steroids including corticosteroids used as an adjunct to beta agonist bronchodilators such as beclomethasone dipropionate, flunisolide, fluticasone, budesonide and triamcinolone acetonide; and also include peptide non-adrenergic non-cholinergic neurotransmitters and anticholinergics. Anti-inflammatory drugs used in connection with the treatment of respiratory diseases include steroids, such as beclomethasone dipropionate, triamcinolone acetonide, flunisolide and fluticasone. Other anti-inflammatory drugs and antiasthmatics include cromoglycates, such as cromolyn sodium. Other respiratory drugs which would qualify as bronchodilators include anticholinergics, such as ipratropium bromide. Other useful respiratory drugs include leukotriene (LT) inhibitors, vasoactive intestinal peptide (VIP), tachykinin antagonists, bradykinin antagonists, endothelin antagonists, heparin furosemide, anti-adhesion molecules, cytokine modulators, biologically active endonucleases and recombinant human (rh) DNase compounds.

The present invention is intended to encompass the free acids, free bases, salts, amines and various hydrated and semi-hydrated forms of such respiratory drugs, and is particularly directed towards pharmaceutically acceptable formulations of such drugs, which are formulated in combination with pharmaceutically acceptable excipient materials generally known to those skilled in the art, preferably without other additives such as preservatives. Preferred drug formulations do not include additional components such as preservatives which have a significant effect on the overall formulation. Thus preferred formulations consist essentially of pharmaceutically active drug and a pharmaceutically acceptable carrier (e.g., water and/or ethanol). However, if a drug is a liquid with a sufficiently low viscosity that it can be aerosolized using a dispenser of the present invention, the formulation may consist essentially of the drug without an excipient.

The terms "aerosol," "bolus," "aerosolized volume of air," and the like, are used interchangeably herein to describe a volume of air greater than 50 ml. and less than 4 liters which has suspended within it particles of a formulation comprising a drug wherein the particles have a diameter in the range of 0.5 to 12 microns, and the total volume of formulation is from 100 $\mu$l to 10,000 $\mu$l. About 10 $\mu$l of particles having a diameter of about 0.5 to 12 microns are present in a volume of about 100 ml to 2 liters, preferably a volume of 200 ml to 1 liter.

The terms "particle free," "bolus," and the like, are used interchangeably herein to describe a volume of air which is substantially free of other material and, in particular, substantially free of particles of drug. The bolus preferably has a volume in the range of 0.05 to 4 liters and is preferably pure air.

The term "dosing event" as used herein means the administration of drug to a patient in need thereof by the intrapulmonary route of administration (i.e., inhaling aerosolized particles into the lung), which event may encompass one or more releases of drug formulation from a drug dispensing device over a period of time of 15 minutes or less, preferably 10 minutes or less, and more preferably 5 minutes or less, during which period multiple inhalations may be made by the patient and multiple doses of drug may be released and inhaled. A dosing event shall involve the administration of drug formulation to the patient in an amount of about 10 $\mu$l to about 1,000 $\mu$l in a single dosing event, which may involve the release of from about 100 $\mu$l to about 10,000 $\mu$l of drug formulation from the device. Because the drug is dissolved in a carrier to form the formulation, the amount of drug delivered may be very small, and will vary with the concentration of drug in the carrier. Accordingly, a dosing event may include the release of drug contained within one of many containers of a package held in a cassette, or the drug contained within a plurality of such containers, when the containers are administered over a period of time, e.g., within 5 to 10 minutes of each other, preferably within 1–2 minutes of each other.

The term "velocity of the drug" or "velocity of particles" means the average speed of particles of the drug formulation moving from a release point, such as a porous membrane or a valve, to a patient's mouth. In a referred embodiment, the velocity of the particles is zero or substantially zero in the absence of flow created by patient inhalation.

The term "bulk flow rate" as used herein means the average velocity at which air moves through a channel, considering that the flow rate is at a maximum in the center of the channel and at a minimum at the inner surface of the channel.

The term "flow boundary layer" means a set of points defining a layer above the inner surface of a channel through which air flows, wherein the air flow rate below the boundary layer is substantially below the bulk flow rate, e.g., 50% or less than the bulk flow rate.

The term "carrier" means a liquid, flowable, pharmaceutically acceptable excipient material in which a drug is suspended, or, more preferably, dissolved. Useful carriers do not adversely interact with the drug, and have properties which allow for the formation of aerosolized particles, preferably particles having a diameter in the range of 0.5 to 12.0 microns when a formulation comprising the carrier and drug is forced through pores having a diameter of 0.25 to 6.0 microns. Preferred carriers include water, ethanol, saline solutions, and mixtures thereof, with pure water being preferred. Other carriers can be used provided that they can be formulated to create a suitable aerosol, and do not adversely affect the drug or human lung tissue.

The term "measuring" describes an event whereby the (1) total lung capacity, (2) inspiratory flow rate or (3) inspiratory volume of the patient is measured and/or calculated and not simply set or controlled. Per the inventive device measuring is carried out and the information used in order to determine an optimal point in the inspiratory cycle at which to release an aerosol and/or a volume of particle free air. An actual measurement of both rate and volume may be made, or the rate can be directly measured and the volume calculated based on the measured rate. The total lung capacity can be measured or calculated based on the patient's height, sex and age. It is also preferable to continue measuring inspiratory flow during and after any drug delivery, and to record inspiratory flow rate and volume before, during, and after the release of drug. Such reading makes it possible to determine if drug was properly delivered to the patient.

The term "monitoring" as used herein means measuring lung functions such as inspiratory flow, inspiratory flow rate, and/or inspiratory volume so that a patient's lung function as defined herein, can be evaluated before and/or after drug delivery, thereby making it possible to evaluate the effect of drug delivery on the patient's lung function.

The term "inspiratory flow rate" means herein a value of air flow rate determined, calculated or measured based on the speed of the air passing a given point in a measuring device, assuming atmospheric pressure ±5% and a temperature in the range of about 10° C. to 40° C.

The term "inspiratory flow" means herein a value of air flow calculated based on the speed of the air passing a given point along with the volume of the air that has passed that point with the volume calculation being based on integration of the flow rate data, assuming atmospheric pressure ±5%, and temperature in the range of about 10° C. to about 40° C.

The term "inspiratory volume" shall mean a determined, measured or calculated volume of air passing a given point into the lungs of a patient, assuming atmospheric pressure ±5%, and a temperature in the range of 10° C. to 40° C.

The term "inspiratory flow profile" means herein data calculated in one or more events measuring inspiratory flow and cumulative volume, which profile can be used to determine a point within a patient's inspiratory cycle which is optimal for the release of drug to be delivered to a patient. An optimal point within the inspiratory cycle for the release of an aerosolized volume of air is based, in part, on (1) a point most likely to deliver aerosolized air to a particular area of a patient's lung, in part on (2) a point within the inspiratory cycle likely to result in the maximum delivery of drug and, in part, on (3) a point in the cycle most likely to result in the delivery of a reproducible amount of drug to the patient at each release of drug. The criteria 1–3 are listed in a preferred order of importance. However, the order of importance can change based on circumstances. The area of the lung being treated is determined by adjusting the volume of aerosol and particle free air and/or by adjusting the particle size of the aerosol. The repeatability is determined by releasing at the same point in the respiratory cycle each time drug is released. To provide for greater efficiency in delivery, the drug delivery point is selected within given parameters.

The term "therapeutic index" refers to the therapeutic index of a drug defined as $LD_{50}/ED_{50}$. The $LD_{50}$ (lethal dose, 50%) is defined as the dose of a drug which kills 50% of the tested animals, and the $ED_{50}$ is defined as the effective dose of the drug for 50% of the individuals treated. Drugs with a therapeutic index near unity (i.e. $LD_{50}/ED_{50}$ is approximately equal to 1) achieve their therapeutic effect at doses very close to the toxic level and as such have a narrow therapeutic window, i.e. a narrow dose range over which they may be administered.

The terms "formulation" and "liquid formulation" and the like are used interchangeably herein to describe any pharmaceutically active respiratory drug with a pharmaceutically acceptable carrier in flowable liquid form having properties such that it can be aerosolized to particles having a diameter of 0.5 to 12.0 microns. Such formulations are preferably solutions, e.g. aqueous solutions, ethanoic solutions, aqueous/ethanoic solutions, saline solutions, colloidal suspensions and microcrystalline suspensions. Formulations can be solutions or suspensions of drug in a low boiling point propellant. Preferred formulations are drug(s) dissolved in water.

The terms "lung function" and "pulmonary function" are used interchangeably and shall be interpreted to mean physically measurable operations of a lung, including but not limited to (1) inspiratory and (2) expiratory flow rates as well as (3) lung volume, i.e., total lung capacity. Methods of quantitatively determining pulmonary function are used to measure lung function. Quantitative determination of pulmonary function may be important when delivering drugs including respiratory drugs in order to direct the aerosolized air to a specific area of the lung and to determine effectiveness. Methods of measuring pulmonary function most commonly employed in clinical practice involve timed measurement of inspiratory and expiratory maneuvers to measure specific parameters. For example, forced vital capacity (FVC) measures the total volume in liters forcefully exhaled by a patient from a deep initial inspiration. This parameter, when evaluated in conjunction with the forced expired volume in one second ($FEV_1$), allows bronchoconstriction to be quantitatively evaluated. A problem with forced vital capacity determination is that the forced vital capacity maneuver (i.e. forced exhalation from maximum inspiration to maximum expiration) largely depends on technique. In other words, a given patient may produce different FVC values during a sequence of consecutive FVC maneuvers. The FEF 25–75 or forced expiratory flow determined over the mid-portion of a forced exhalation maneuver tends to be less technique dependent than the FVC. Similarly, the $FEV_1$ tends to be less technique dependent than FVC. In addition to measuring volumes of exhaled air as indices of pulmonary function, the flow in liters per minute measured over differing portions of the expiratory cycle can be useful in determining the status of a patient's pulmonary function. In particular, the peak expiratory flow, taken as the highest air flow rate in liters per minute during a forced maximal exhalation, is well correlated with overall pulmonary function in a patient with asthma and other respiratory diseases. The present invention carries out treatment by administering drug in a drug delivery event and monitoring lung function in a monitoring event. A series of such events may be carried out and repeated over time to determine if lung function is improved.

Each of the parameters discussed above is measured during quantitative spirometry. A patient's individual performance can be compared against his personal best data, individual indices can be compared with each other for an individual patient (e.g. $FEV_1$ divided by FVC, producing a dimensionless index useful in assessing the severity of acute asthma symptoms), or each of these indices can be compared against an expected value. Expected values for indices derived from quantitative spirometry are calculated as a function of the patient's sex, height, weight and age. For instance, standards exist for the calculation of expected indices, and these are frequently reported along with the actual parameters derived for an individual patient during a monitoring event, such as a quantitative spirometry test.

The term "substantially dry" means herein that particles of formulation include an amount of carrier (e.g., water or ethanol) which is equal to (in weight) or less than the amount of drug in the particle, more preferably it means free water is not present.

The term "respiratory disease" means any pulmonary disease or impairment of lung function. Such diseases include restrictive and obstructive disease, and diseases such as emphysema that involve abnormal distension of the lung, frequently accompanied by impairment of heart action. Restrictive diseases tend to limit the total volume of air that a patient is able to exchange through inspiration and expiration. Restrictive disease, such as can be present in certain types of fibrotic processes, can therefore be detected by reduced FVC indices. Obstructive disease, such as is present in patients with asthma, tends not to affect the total volume of air exchangeable through inspiration and expiration, but rather the amount of time required for forced exhalation of air. In particular, the $FEV_1$ is markedly reduced in patients with acute asthma symptoms. More specifically, the $FEV_1$, when taken as a ratio of FVC (i.e. $FEV_1$ divided by FVC), is markedly reduced in patients with acute asthma. In addition to increasing the amount of time required for a full forced expiration, the presence of acute bronchoconstrictive disease tends to decrease the peak expiratory flow measured over a typical forced exhalation. The respiratory disease is understood to be "treated" if lung function is improved, even if the improvement is temporary.

The terms "aerosol particles", "particles", "aerosolized particles of formulation" and the like as used herein mean particles of formulation comprised of pharmaceutically active respiratory drug and carrier, which are formed upon forcing the formulation through a nozzle, which nozzle is preferably in the form of a flexible porous membrane. The particles have a sufficiently small size that, when the particles are formed, they remain suspended in the air for a sufficient amount of time for the patient to inhale the particles into the patient's lungs. For intrapulmonary delivery the particles have a size in the range of 0.5 micron to about 12 microns more preferably 1–4 microns. For nasal or ocular delivery the particles can be larger e.g., up to 40 microns in diameter.

GENERAL OVERVIEW OF THE METHODOLOGY OF THE INVENTION

The invention provides a means to deliver any type of drug to a patient preferably by the intrapulmonary route (but including nasal and ocular delivery) in the form of an aerosol having a desired aerosol particle size and having substantially no undesirable, unsuspended drug particles within the aerosol that would substantially affect the accuracy of the dose of drug delivered in the aerosol. The method of generating an aerosol according to the invention provides a means to generate a reproducibly desirable dose of aerosol for therapeutic and diagnostic applications. Moreover, certain embodiments of the devices and methodology used do not require the release of low boiling point propellants in order to aerosolize drug, which propellants are conventionally used in connection with hand-held metered dose inhalers. However, like conventional hand-held metered dose inhalers, the devices used in conjunction with the present invention are hand-held, self-contained, highly portable devices that provide a convenient means of delivering drugs to a patient via the intrapulmonary route. In general, an aerosol for intrapulmonary delivery is generated from a drug formulation, preferably a flowable formulation, more preferably a liquid (at a temperature of 10° C. to 30° C.), flowable formulation. The drug formulation can be contained within a multi-dose container or within a container portion of a disposable package, where the container of the disposable package has at least one surface that is collapsible. The aerosol is generated by applying pressure (preferably less than 50 bar) to the collapsible container surface, thereby forcing the contents of the container through a low resistance filter and then through a porous membrane. The porous membrane may be rigid or flexible. Preferably the porous membrane is flexible so that upon application of the pressure required to aerosolize the drug formulation (i.e., preferably 50 bar or less, more preferably 35 bar or less), the porous membrane becomes convex in shape, thus delivering the aerosolized drug into the flow path of the drug delivery device in a region beyond the flow boundary layer. The low resistance filter has a pore density and pore size the same as or greater than the pore density and pore size of the porous membrane. The low resistance filter thus prevents drug particles of an undesirable size from reaching the porous membrane, and filters out such undesirable particles before the aerosol is generated for delivery. The pore size and pore density are adjusted so that formulation in the container is aerosolized in a short period (e.g. 1 sec or less) without the need for a large amount of pressure such as would rupture the container or membrane (e.g. less than 50 bar).

The formulations for use in the present invention can include preservatives or bacteriostatic type compounds. However, the formulation preferably consists essentially only of a pharmaceutically active drug and pharmaceutically acceptable carrier i.e., does not include other components which are intentionally added. The formulation can be primarily or essentially composed of the drug (i.e., without carrier) if the drug is freely flowable and can be aerosolized. Useful formulations can comprise formulations currently approved for use with nebulizers as well as those for nasal sprays and ocular drops. However, nebulizer formulations must, in general, be diluted prior to administration. The formulations are sterilized and placed in individual containers in a sterile environment.

Further the drug dispensing device of the present invention preferably includes electronic and/or mechanical components which eliminate direct actuation of drug release by the user. More specifically, the device preferably includes a means for measuring inspiratory flow rate and inspiratory volume and sending an electrical signal as a result of the simultaneous measurement of both (so that drug can be released at the same point each time), and also preferably includes a microprocessor programmed to receive, process, analyze and store the electrical signal of the means for measuring flow. Upon receipt of signal values within appropriate limits, the microprocessor sends an actuation signal to the mechanical means thereby causing drug to be extruded from the pores of the porous membrane. Thus, since preferred embodiments of the devices used in connection with the present invention include a means of analyzing breath flow and a microprocessor capable of making calculations based on the inhalation profile, the present invention can provide a means for repeatedly (1) dispensing and (2) delivering the same amount of the drug to a patient at each dosing event.

The present invention includes at least six distinct aspects which include (1) a disposable package, (2) a cassette which includes a plurality of packages, (3) a drug dispensing device which can be loaded with a cassette, (4) a drug delivery device that can be loaded with a ribbon of low resistance filters and/or a ribbon of porous membranes and used in conjunction with a disposable package or a multi-dose container, (5) a drug dispensing device with a cam assembly for automatic extrusion of the formulation from the disposable package at a predetermined pressure, and optional means for exchange of an emptied package in a cassette with a fresh loaded drug package, (7) a method of generating an aerosol and (6) a method of drug delivery.

The invention will now be described in more detail.

CONTAINERS OF THE INVENTION

In general, any container can be used in conjunction with the low-resistance filter and porous membrane according to the invention. The container can be, for example, a single-dose container or a multi-dose container. The drug containers can be refillable or reusable but are preferably single use disposable containers. The container can be designed for storage and delivery of a drug that is dry, substantially dry, liquid, or in the form of a suspension. The drug container may be any desired size. In most cases the size of the container is not directly related to the amount of drug being delivered in that formulations can include relatively large amounts of excipient material, e.g., water or a saline solution. Accordingly, a given size container could include a wide range of different doses by varying drug concentration.

Drug containers can include indices which can be electronic and can be connected to a power source such as a battery. The indices can be in the form of visually perceivable numbers, letters or any type of symbol capable of conveying information to the patient. Alternatively, the indices can be connected to a power source such as a battery when the indices are in the form of magnetically, optically or electronically recorded information that can be read by a drug dispensing device, which in turn provides visual or audio information to the user. The indices can be designed for any desired purpose but in general provide specific information relating to the day and/or time the drug within a container should be administered to the patient. Such indices can record, store, and transfer information to a drug dispensing device regarding the number of doses remaining in the container. The containers can include labeling, which can be in any format and could include days of the month or other symbols or numbers in any variation or language.

In addition to disclosing specific information regarding the day and time for drug delivery, the indices can provide more detailed information such as the amount of drug dispensed from each container. This information might be particularly useful if the containers include different amounts of drug. Further, magnetic, optical and/or electronic indices can have new information recorded onto them, which information could be placed there by the drug dispensing device. For example, a magnetic recording means can receive information from the drug dispensing device indicating the precise time the drug was actually administered to the patient. In addition to recording the time of delivery, the device can monitor the expected efficacy of the delivery based on factors such as the inspiratory flow rate that occurred following the initial release of drug. The information recorded can then be read by a separate device, interpreted by the care-giver, and used to determine the usefulness of the present treatment methodology. For example, if the patient did not appear to be responding well, and the recorded information indicated that the patient had taken the drug at the wrong time, or that the patient had misdelivered drug by changing inspiratory flow rate after initial release, it might be determined that further education in patient use of the device was needed, but that the present dosing methodology might well be useful. However, if the recordings indicated that the patient had delivered the drug using the proper techniques and still had not obtained the correct results, a different drug or dosing methodology might be recommended.

The container can also be one that provides for storage of a drug in a dry or substantially dry form until the time of administration, at which point, if desired, the drug can be mixed with water or other liquid. A dual compartment container for carrying out such mixing of dry drug with liquid just prior to administration is described in U.S. Pat. No. 5,558,085, issued Sep. 24, 1996, incorporated herein by reference with respect to such containers.

In one embodiment, the drug container is a multi-dose container, preferably a disposable multi-dose container. Multi-dose containers that can be used with the present invention can be a conventional canister containing the medication to be delivered and a suitable propellant or carrier for the mediation and having a valve for controlling the release of medication when the valve is depressed and thus opened. Such canisters are commercially available from a variety of sources, and are well known in the art. One such canister is model No. C-128-S available from Prespart Co., and one suitable valve for that canister is a straight valve model No. BK-295, available from BESPAK, King's Lynn, England. The use of a multi-dose canister as a drug container in a drug delivery device useful in the present invention is described in U.S. Pat. No. 5,404,871, issued Apr. 11, 1995; U.S. Pat. No. 5,394,866, issued Mar. 7, 1995; and U.S. Pat. No. 5,608,647, issued Mar. 4, 1997, incorporated herein by reference with respect to the configuration and use of such multi-dose containers in a drug delivery device.

In a preferred embodiment, the containers useful with the invention comprise a single-use, single-dose, disposable container that holds a formulation for delivery to a patient.

The preferred container has a collapsible wall. In addition, the container can be configured in the same package with a porous membrane and a low resistance filter, where the low resistance filter is positioned between the porous membrane and a formulation contained in the container. The container is preferably disposable after a single use in the delivery of the formulation contained therein.

The drug container can be of any desired size. In most cases the size of the container is not directly related to the amount of drug being delivered in that most formulations include relatively large amounts of excipient material, e.g., alcohol, (e.g., ethanol with or without water) water or a saline solution. Accordingly, a given size container could include a wide range of different doses by varying drug concentration.

Drug containers may include indices, which may be electronic and may be connected to a power source such as a battery. The indices can be in the form of visually perceivable numbers, letters, or any type of symbol capable of conveying information to the patient. Alternatively, the indices can be connected to a power source such as a battery when the indices are in the form of magnetically, optically or electronically recorded information that can be read by a drug dispensing device, in turn providing visual or audio information to the user. The indices can be designed for any desired purpose but in general provide specific information relating to the day and/or time the drug within a container should be administered to the patient. Such indices may record, store, and transfer information to a drug dispensing device regarding the number of doses remaining in the container. The containers may include labeling, which can be in any format, and could include days of the month or other symbols or numbers in any variation or language.

In addition to disclosing specific information regarding the day and time for drug delivery, the indices could provide more detailed information, such as the amount of drug dispensed from each container. Such information might be particularly useful if the containers included different amounts of drug. Further, magnetic, optical and/or electronic indices could have new information recorded onto them by the drug dispensing device. For example, a magnetic recording means could receive information from the drug dispensing device indicating the precise time the drug was actually administered to the patient. In addition to recording the time of delivery, the device could monitor the expected efficacy of the delivery based on factors such as the inspiratory flow rate immediately following the initial release of drug. The volume of aerosolized and unaerosolized air released is also recorded. The information recorded could then be read by a separate device, interpreted by the care-giver, and used to determine the usefulness of the present treatment methodology. For example, if the patient did not appear to be responding well, but the recorded information indicated that the patient had taken the drug at the wrong time or that the patient had misdelivered drug by changing inspiratory flow rate after initial release, it might be determined that further education in patient use of the device was needed, but that the present dosing methodology might well be useful. However, if the recordings indicated that the patient had delivered the drug using the proper techniques and still had not obtained the correct results, a different drug or dosing methodology (e.g., changing the volume of aerosolized or unaerosolized air released) might be recommended.

FIG. 1 is a cross-sectional view of a disposable container 1 of the invention which is shaped by a collapsible wall 2. The container 1 has an opening covered by a flexible porous membrane 302, which is covered by a removable layer 4. The membrane 302 may be rigid and protrude upward in a convex configuration away from the formulation 5. A low resistance filter 301 is positioned between the formulation 5 and the porous membrane 302. The filter 301 has pores of a diameter and are present at a pore density such that the presence of the filter 301 does not substantially increase the pressure required to generate an aerosol when the formulation is forced through the porous membrane. When the layer 4 is removed, the wall 2 can be collapsed, thereby forcing the respiratory drug formulation S through the low resistance filter 301 and through the flexible porous membrane 302, which will then protrude outward in a convex shape.

Figure 2:
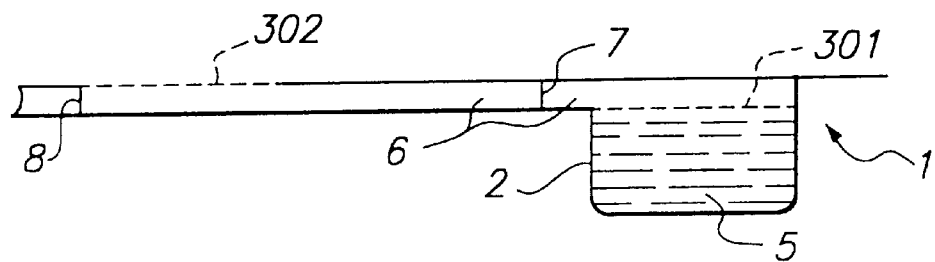
FIG. 2 is a cross-sectional view of a preferred embodiment of a container used in carrying out the invention.

FIG. 2 is a cross-sectional view of a more preferred embodiment of a disposable container 1 of the invention. The container is shaped by a collapsible wall 2. The container 1 includes an opening which leads to an open channel 6 which channel 6 includes an abutment (or burstable seal) 7 which is broken upon the application of force created by formulation 5 being forced from the container by extrusion cam 9. The low resistance filter 301 is positioned between the formulation 5 and the burstable seal 7. When the abutment 7 is broken, the formulation 5 flows through the opening to an area adjacent to the flexible porous membrane 302 and is prevented from flowing further in the channel 6 by a non-breakable abutment 8.

Figure 3:
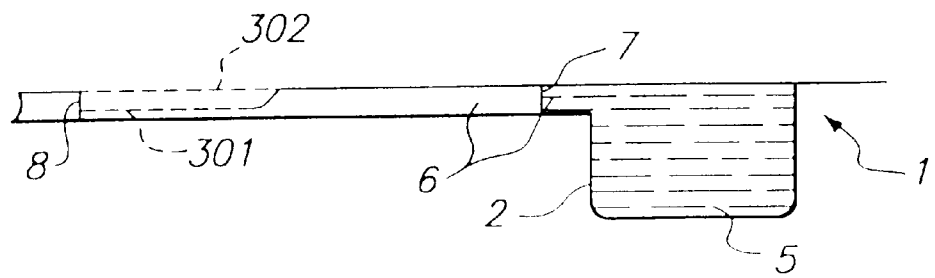
FIG. 3 is a cross-sectional view of a container of a preferred embodiment of a container used in carrying out the invention.

FIG. 3 is a cross-sectional view of another preferred embodiment of a disposable container 1 of the invention. The container is shaped by a collapsible wall 2. The container 2 includes an opening 54 that leads to an open channel 6, which channel 6 includes an abutment (or burstable seal) 7, which is broken upon the application of force created by formulation 5 being forced from the container. The low resistance filter 301 is positioned between the burstable seal 7 and the porous membrane 302. When the burstable seal 7 is broken, the formulation 5 flows to an area adjacent the low resistance filter 301, through the low resistance filter 301, and out the porous membrane 302 to form an aerosol. The formulation 5 is prevented from flowing further in the channel 6 by a non-breakable abutment 8.

Figure 4:
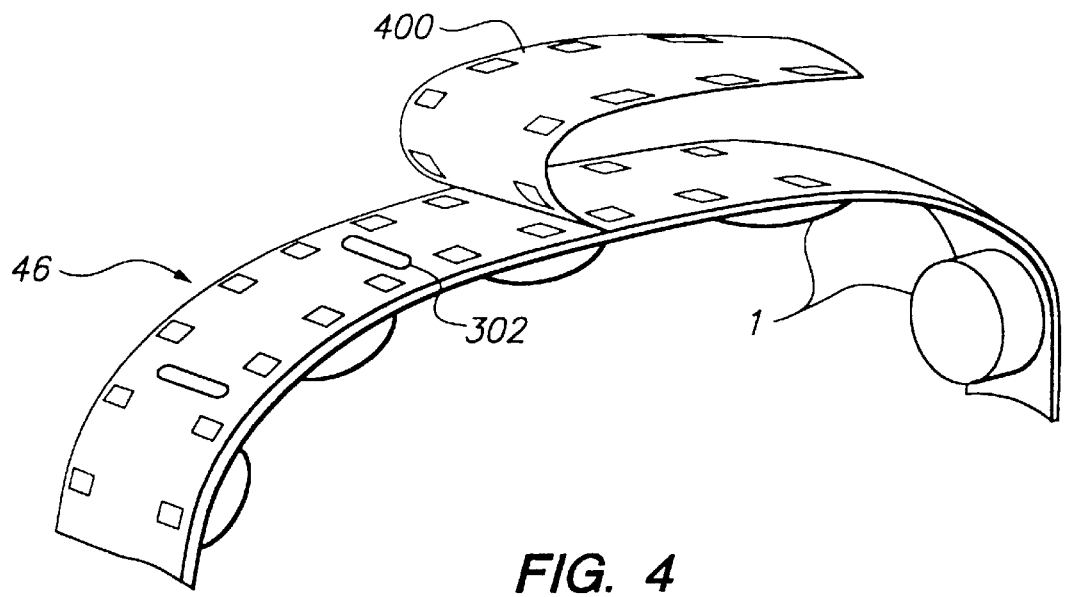
FIG. 4 is a perspective view of a disposable package of the invention.

A number of containers can be connected together to form a package 46 as shown in FIG. 4. The package 46 is shown in the form of an elongated tape, but can be in any configuration (e.g. circular, square, rectangular, etc.). An individual container shown in FIG. 5 includes an opening 80 covered by a convex shaped membrane 302.

Figure 6:
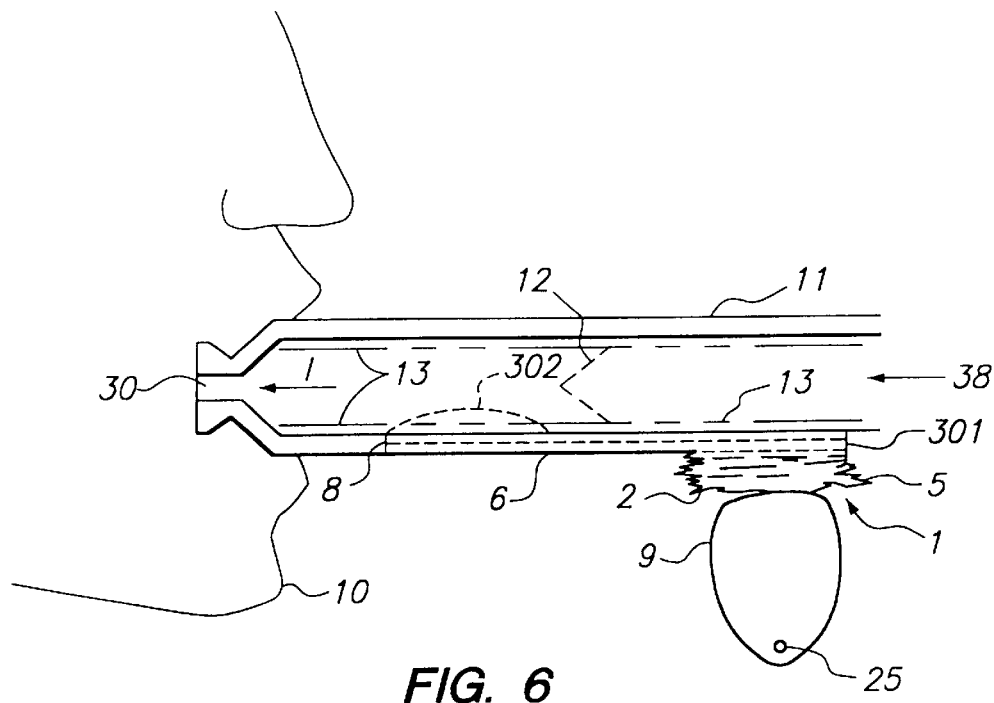
FIG. 6 is a cross-sectional view of the container of FIG. 2 in use in a channel of a drug delivery device.

FIG. 6 is a cross-sectional view of the disposable container 1 of FIG. 2 in use. The wall 2 is being crushed by a mechanical component such as an extrusion cam 9 attached to the cam shaft 25 of a cam assembly 24. The cam shaft 25 is driven by a motor (not shown), which can be connected to gears (not shown) that move the cam shaft 25 so as to turn the extrusion cam 9, bringing cam 9 into contact with and applying a force (preferably force of up to 50 bar but not including, 50 bar), to the collapsible wall 2 so as to collapse wall 2 of the container 1. Due to the collapse of wall 2, the formulation 5 is forced through the low resistance filter 301, into the open channel 6 (breaking the abutment 7 shown in FIG. 2), and against and through the membrane 302 causing the membrane 302 to protrude outward into a convex configuration as shown in FIG. 3. The cam 9 has been forced against the container wall 2 after a patient 10 begins inhalation in the direction of the arrow "I". The patient 10 inhales through the mouth from a tubular channel 11. The velocity of the air moving through the flow path 29 of the channel 11 can be measured across the diameter of the channel to determine a flow profile 12, i.e., the air flowing through the channel 11 has a higher velocity further away from the inner surface of the channel. The air velocity immediately adjacent to the inner surface of the channel 11 (i.e., infinitely close to the surface) is very slow (i.e., approaches zero). A flow boundary layer 13 defines a set of points below which (in a direction from the channel center toward the inner surface of the channel) the flow of air is substantially below the bulk flow rate, i.e., 50% or less than the bulk flow rate.

Figure 5:
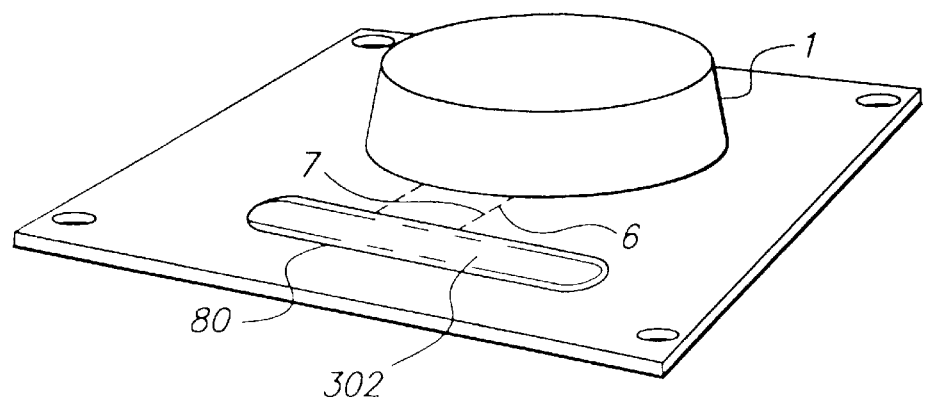
FIG. 5 is a overhead perspective view of a preferred embodiment of a container of the invention.

As shown in FIG. 6 the convex shape that the flexible porous membrane 302 takes on during use plays an important role. The membrane 302 may be rigid and convex; and a rigid convex membrane 80 is shown in FIG. 5. Preferably, the upper surface of the flexible porous membrane 302 is substantially flush with (i.e., in substantially the same plane as) the inner surface of the channel 11 to allow air to flow freely. Thus, if the membrane 302 remained in place when the formulation 5 moved through the pores, the formulation would be released into the slow moving or substantially "dead air" below the boundary layer 13. However, when the formulation 5 is forced from the container 1 by force applied from a source such as a motor-driven cam 9, the formulation 5 presses against a flexible porous membrane 302 causing it to convex outward beyond the plane of the resting surface of the membrane 302 and beyond the plane of the inner surface of the channel 11. The convex upward distortion of the membrane 302 is important because it positions the pores of the membrane beyond the boundary layer 13 (shown in FIG. 6) into faster moving air of the channel 29.

When pores of the membrane 302 are positioned beyond the boundary layer 13 into the faster moving air of the channel advantages are obtained. Specifically, the (1) formulation exiting the pores is moved to an air stream where it can be readily carried to the patient and (2) the particles formed do not exit into slow moving or "dead" air, and thus do not rapidly decelerate to a degree such that particles behind them catch up with, collide into and merge together. Such collisions are not desirable because they (a) result in particles which are too large and cannot be efficiently inhaled into the lung (e.g. through agglomeration of particles); and (b) result in an aerosol with diverse and unpredictable particle sizes.

More specifically, when formulation exits the pores the formulation naturally forms spherical particles. Those particles slow down due to the frictional resistance created by the air through which the particles must travel. The particles behind them can face reduced air friction because the preceding particles have moved the air aside. Thus later released particles catch up with and merge into the earlier released particles. This can cause a chain reaction resulting in the formation of particles too large to be readily inhaled into the lung—e.g., the formation of particles having a diameter of more than about 12.0 microns. Thus (a) or (b) or both phenomena can result in erratic dosing.

USE OF THE LOW RESISTANCE FILTER AND THE POROUS MEMBRANE WITH SINGLE-DOSE AND MULTI-DOSE CONTAINERS

In another embodiment of the invention, the drug delivery device and method for generation of inhalable aerosols by extrusion through a porous membrane useful in the present invention are described in the copending U.S. application entitled "Anti-Clogging Nozzle for Generating Inhalable Aerosol," U.S. Ser. No. 08/804,041, filed Feb. 24, 1997, now U.S. Pat. No. 5,829,435 issued Nov. 3, 1998, which application is incorporated herein by reference in its entirety and which application discloses an invention invented under an obligation to assign rights to the same entity to which the rights in the present invention were invented under an obligation to assign. Briefly, the drug delivery devices and methods described therein involve the use of a drug delivery device that uses a low resistance filter and a porous membrane to prevent the passage of undissolved particles or drug and/or other undesirable particles from being delivered to the patient. In general, the drug formulation is released from a container, passed through at least one low resistance filter, and then passed through a porous membrane. An aerosol is formed from the drug formulation when it exits the pores of the porous membrane, and the aerosol is delivered to the patient. Thus, it is important that the drug formulation pass through the low resistance filter before the formulation passes through the porous membrane and before an aerosol is formed from the formulation.

The low resistance filter and the porous membrane can be included as components of a disposable package that is composed of a container that serves as a storage receptacle for the drug formulation, a porous membrane, and a low resistance filter positioned between the drug formulation and the porous membrane. Such packages and drug containers are described in detail below.

The low resistance filter and the porous membrane can also be provided separately from the drug container and/or the disposable package. For example, the low resistance filter can be provided as a single disposable filter that can be inserted the device in a position between the formulation in the container and a porous membrane, which can also be provided as a single disposable membrane. The disposable filter and disposable membrane can be inserted prior to use and then disposed of after each use, or after a recommended number of uses. Alternatively, the low resistance filter and porous membrane can be provided as a separate ribbon or ribbons, as shown in FIGS. 7 and 8.

Figure 7:
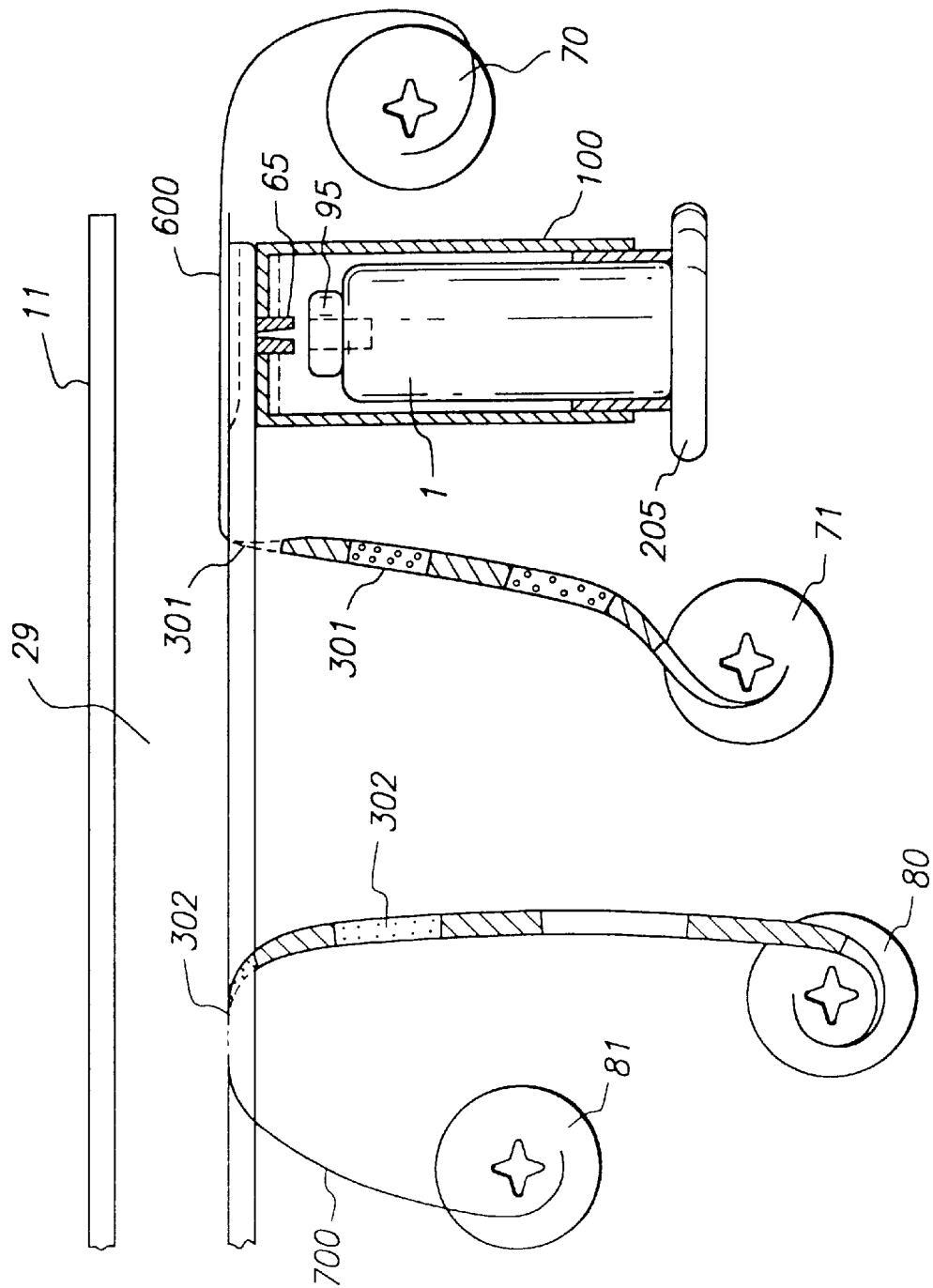
FIG. 7 is a cross-sectional view of a drug delivery device of the invention having a multi-dose container and a ribbon of low resistance filters and a ribbon of porous membranes.

FIG. 7 shows a cross-sectional view of a drug delivery device having a multi-dose container 1. The device is shown with a holder 100 having cylindrical side walls and a removable cap 205. The holder 100 is "loaded" in that it includes a multi-dose container 1 (e.g., a pressurized multi-dose canister). The container 1 includes a valve which is preferably a non-metering valve 95, which is held down in the open position when the cap 205 is closed (e.g., screwed down), thus setting the valve 95 into a seat 65, which is in connection with a flow path 29. The device additionally comprises a ribbon 600 that comprises a plurality of low-resistance filters 301 that are interconnected to each other and are preferably held in the ribbon 600 in an organized manner, e.g., interfolding or wound, thus making it possible to move the individual filters 301 into a position for filtering the drug formulation during drug delivery within the device. In a similar manner, a second ribbon 700 comprises a plurality of porous membranes 302 that are interconnected to each other, and are preferably held in the second ribbon 700 in an organized manner, e.g., interfolding or wound, thus making it possible to move the individual porous membranes 302 into a position for generating an aerosol from the drug formulation during drug delivery using the device. Although it is possible to rewind any used portion of the filter ribbon and/or the membrane ribbon on sprockets 70,71 and 80,81, respectively, or randomly fold it into a compartment, it is also possible to disperse the used portion outside of the device 40 and immediately dispose of such. The device can alternatively be configured so that the low-resistance filters 301 are provided in a ribbon 600 as shown in FIG. 7 and the porous membrane 302 is provided as a single permanent or disposable portion of the device, or vice versa.

Figure 8:
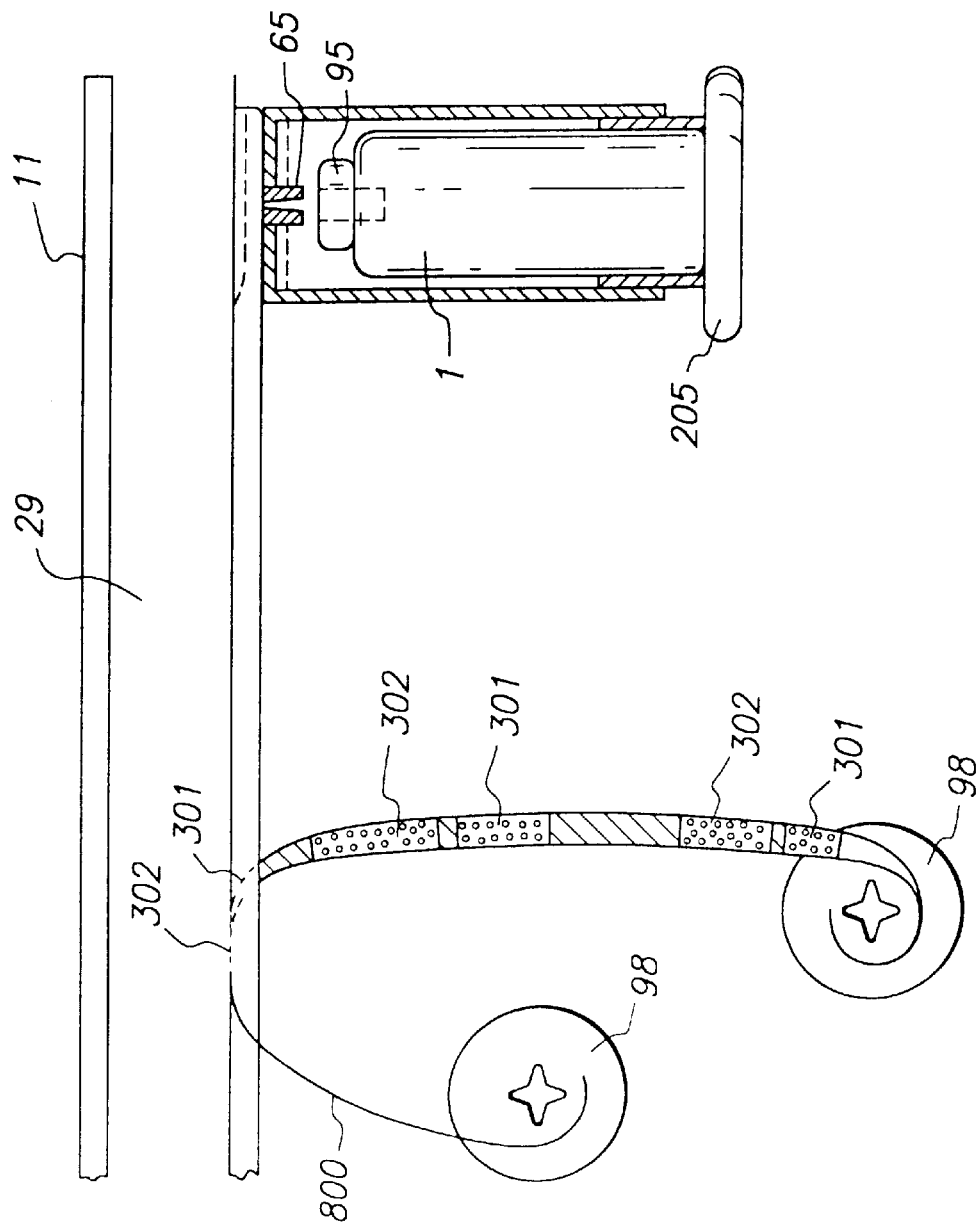
FIG. 8 is a cross-sectional view of a drug delivery device of the invention having a multi-dose container and single ribbon having both interconnected low resistance filters and porous membranes.
Figure 10:
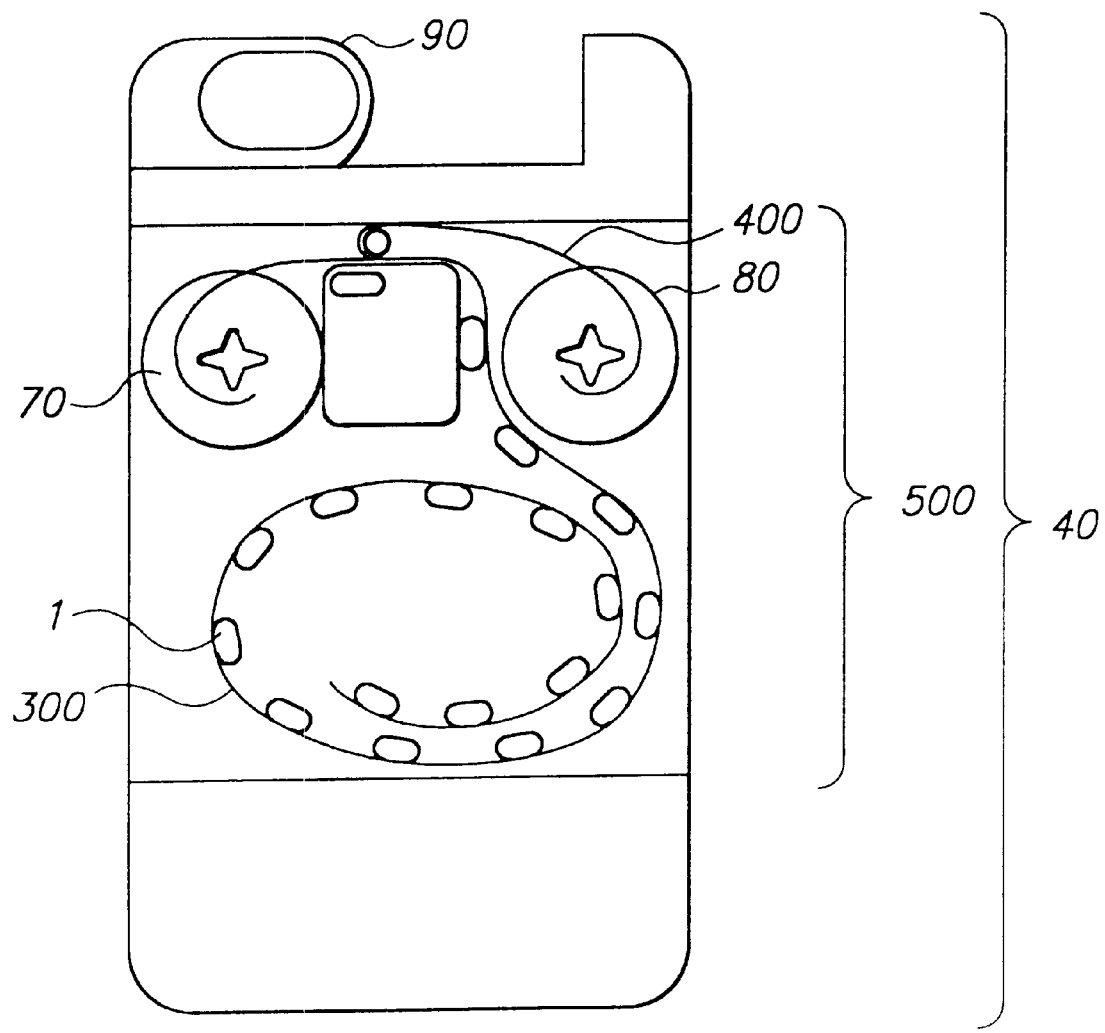
FIG. 10 is a cross-sectional view of drug delivery device of the invention loaded with a cassette.

Alternatively, as shown in FIG. 8, the low resistance filter 301 and porous membrane 302 can be provided within a single ribbon 800. The low resistance filters 301 and porous membranes 302 are interconnected one to another in such a manner that the ribbon 800 is positioned within the device to provide a low resistance filter 301 between the drug formulation container 1 and a porous membrane 302 during drug delivery from the container 1. The ribbon 800 is preferably configured within the device in an organized manner, e.g., interfolding or wound (e.g., on sprockets 98), thus making it possible to move the individual filters 301 and porous membranes 302 into a position for filtering and aerosolizing the drug formulation during drug delivery within the device. Although the embodiments of the invention shown in FIGS. 7 and 8 use a multi-dose container, ribbons that have low-resistance filters, porous membranes, or both, can also be used in conjunction with disposable, containers, e.g., as shown in FIGS. 1–6.

DRUG AND DIAGNOSTIC FORMULATIONS

The drug or diagnostic compound that is released to the patient may be in a variety of different forms. Preferably, the formulation is in the form of a flowable formulation, more preferably a liquid, flowable formulation. For example, the drug or diagnostic may be an aqueous solution of drug, i.e., drug or diagnostic dissolved in water and formed into small particles to create an aerosol, which is delivered to the patient by the device. Alternatively, the compound may be in a solution wherein a low-boiling point propellant is used as a solvent. In yet another embodiment, the compound may be in the form of a dry powder that is intermixed with an airflow in order to provide for particlized delivery of compound to the patient.

Regardless of the type of compound or the form of the formulation, it is preferable to create aerosol particles having a size in the range of about 0.5 to 12 microns. The particles may be released at one size and thereafter reduced in size via evaporation through heating. The compound can be directed to a particular area of the lung which needs treatment by adjusting the aerosol particle size. By creating aerosol particles which have a relatively narrow range of size, it is possible to further increase the efficiency of the delivery system and improve the repeatability of the dosing. Thus, it is preferable that the particles not only have a size in the range of 0.5 to 12 microns, but that the mean particle size be within a narrow range, so that 80% or more of the particles being delivered to a patient have a particle diameter that is within ±20% of the average particle size, preferably within ±10%, and more preferably within ±5% of the average particle size.

The formulation may be a low viscosity liquid formulation. The viscosity of the drug or diagnostic by itself or in combination with a carrier is not of particular importance except to note that the formulation must have characteristics such that the formulation can be forced out of openings to form an aerosol, e.g., when the formulation is forced through the flexible porous membrane it will form an aerosol preferably having a particle size in the range of about 1 to 12 microns, more preferably of about 3.0 to 6.0 microns.

AEROSOL DELIVERY DEVICES

A drug delivery device 40 of the present invention is shown in FIG. 9. The device 40 includes a channel 29 opened at a first end or mouthpiece 30 for a patient to withdraw aerosolized formulation after the channel has received aerosolized formulation. The device includes an electric motor 28 and a camshaft 25 mechanically connected to the motor. The device also includes a container holding means which as shown in FIG. 9 includes the vibration devices 45 which hold the container in an aerosol release position. Lastly, the device includes an extrusion cam 22 positioned on the camshaft 25. The cam 22 is configured such that upon rotation of the camshaft the surface of the cam is moved towards the drug release position. When the cam has moved fully into the drug release position the contents of the container 2 is forced out of the porous membrane 301 and into the channel 29.

An exemplary device 40 of the invention is shown in FIG. 9. The device 40 is a hand held, self-contained, portable, breath-actuated inhaler device 40 having a holder 20 with cylindrical side walls and a hand grip 21. The holder 20 is "loaded," i.e. connected to a container 1 that includes drug dosage units having liquid, flowable formulations of pharmaceutically active drug therein. A plurality of containers 1 (2 or more) are preferably linked together to form a package 46.

FIG. 10 is a cross-sectional view of a cassette 500 loaded into a drug delivery device 40. The disposable package 46 is folded or wound into the cassette 500 in a manner which makes it possible to move the individual containers 1 into an aerosol release position within the device 40. Although it is possible to rewind any used portion of the package on a sprocket 70 and rewind the used cover 400 on a sprocket 80 or randomly fold it into a compartment, it is also possible to disperse the used portion outside of the cassette 500 and device 40 and immediately dispose of such.

Although the device 40 shown in FIG. 10 includes a mouthpiece 90 shown here as rotatably attached thereon, it is possible to reconfigure the components so that the mouthpiece 90 is part of and integral with the cassette 500. This arrangement of components makes it possible to dispose of the mouthpiece with the cassette 500 when all the containers 1 on the package 46 have been emptied. The entire device 40 is self-contained, light weight (less than 1 kg, preferably less than 0.5 kg loaded) and portable. The device 40 can be manually or automatically actuated and loaded.

In general, any mechanical means for holding the disposable package and applying the necessary force to the collapsible wall of the container to move the formulation through the low resistance filter and through the porous membrane to generate an aerosol can be used with the present invention. The device for holding the disposable package may be nothing more than a narrow opening comprising an aerosol release position created between two outwardly extending bars 42 and 82 (FIG. 9) or may include additional components for moving new loaded containers in a multi-container package into the release position.

A specific example of a means for moving an empty container out of the release position and a new container into the release position is shown within FIG. 11 in the form of an engagement claw 52. As shown in FIG. 11 the claw 52 can move into an opening on the package 46. When the shaft 25 is rotated the claw is caused to move forward as shown in FIG. 12 thereby moving the package 46. The means for moving the package can be other components such as one or more wheels, sprockets or rollers notably mounted on the end(s) of such bars. The rollers may be spring mounted so as to provide constant pressure against the surface(s) of the package. The device may also include a transport mechanism which may include providing drive power to the roller(s) so that when they are rotated, they remove an emptied container of the package away from the drug release position 17 and advance a loaded container in the package into the drug release position. The power source 43 driving the roller(s) is programmed via the microprocessor 26 to rotate the rollers only enough to move an emptied container of package 39 from the drug release position and another, loaded container into position. The power source 43 can be any convention source of electric power capable of providing electrical power, but is preferably a light weight battery, such as one or more standard alkaline batteries.

Figure 9:
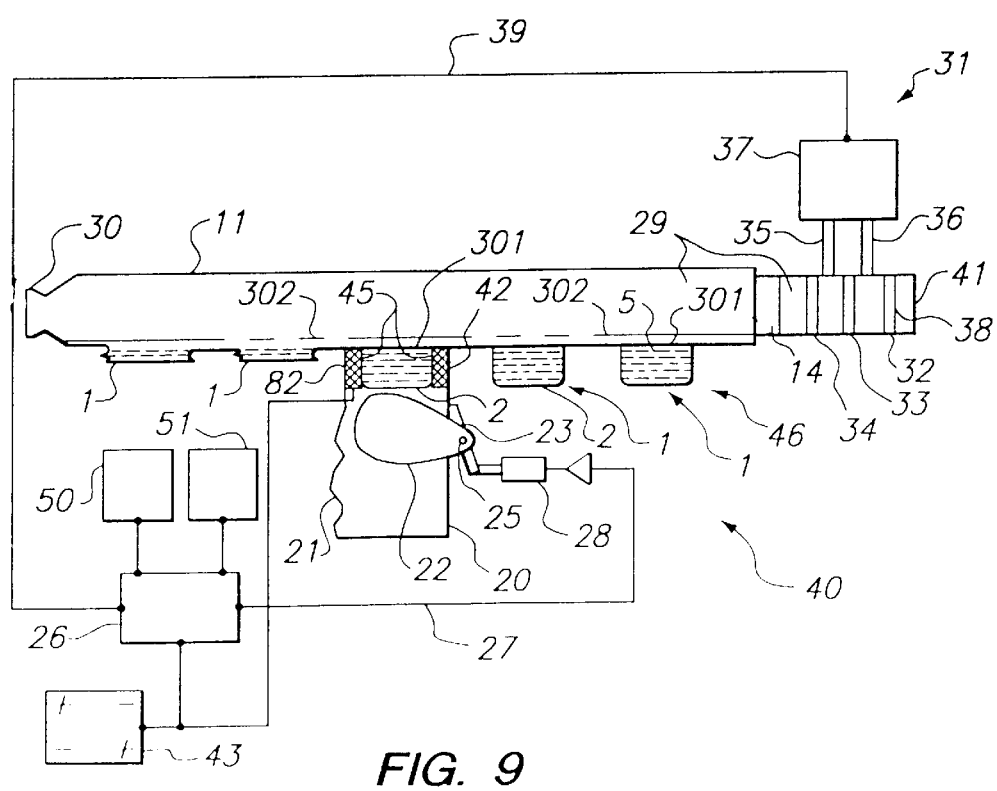
FIG. 9 is a cross-sectional view of a drug delivery device of the invention loaded with a package as shown in FIG. 4.

Preferably, the mechanical means that applies the necessary force (e.g., less than 50 bar), preferably 35 up to, but not including, 50 bar, to the collapsible container wall is a cam, e.g., a motor-driven cam 22 as shown in FIG. 9. The embodiment shown in FIG. 9 is a version of the invention in which the user actuates the device 40 by inhalation from the patient which results in a signal being sent to a motor 28 which turns a motor driven cam 22, and the cam 22 is forced against a collapsible wall 2 of a container 1. When the container 1 is compressed its contents are forced out through the low resistance filter 301 through the membrane 302, and aerosolized. Two additional containers 1 shown to the left are unused. The amount of force sufficient to generate the aerosol is preferably 35 up to, but not including, 50 bar. The device of FIG. 9 would not require the use of low boiling point propellants such as low boiling point fluorocarbons.

THE CAM SHAFT ASSEMBLY

In one preferred embodiment, the device of the invention as described with respect to FIG. 9 above provides a means for extruding the drug formulation from the container into the open channel 29, where it mixes with air inhaled into the channel and can be withdrawn by the patient from the opposite open end. Preferably the drug container 1 is one of a plurality of disposable drug containers in a package 46.

FIGS. 11, 12, 13 and 14 show the extrusion mechanism in the form of a motor-driven cam assembly 24 with an extrusion cam 22 that actuates a mechanism, such as a reciprocating piston 38, for forcing the contents of a container 1 (on the package 46) held at the drug release position through an opening in the periphery of the wall 2 of the container 1 formed by action of the pressure exerted by the extrusion cam. For instance, the collapsible wall 2 of the container can form a jointure with the cover portion 4 (shown in FIG. 1) with the porous membrane 302 situated along a portion of the jointure as shown in FIG. 5. In the aerosol release position, the container 1 is located with respect to the extrusion mechanism such that the collapsible wall 2 of the container 1 is contacted by the extrusion mechanism and the portion of the jointure having the porous membrane is situated in fluid communication with the third opening in the wall 11 leading to the channel 29. Upon application of pressure by the extrusion mechanism the contents of the container is forced out of the container through the membrane and aerosolized in the channel 29.

Referring to FIG. 9 the contents of the container is passed through a low resistance filter 301 and a porous membrane 302, and from thence into the channel 29 through the third opening 18.

In operation, the cam assembly reliably expels the formulation from the container at a uniform rate by repeatedly applying force in the same pressure application cycle to the collapsible wall 2 of each container. The maximum amount of pressure applied by the extrusion cam is preferably less than 50 bar. Thus, the extrusion mechanism differs from a mechanism, such as a spring, that loses resilience over time, and thus may apply a diminishing amount of force to successive containers.

The cam assembly of FIGS. 11–14 preferably further includes a clamping cam 44 attached to a cam shaft 25, which clamping cam 44 forces a clamping member 47 (configured to correspond to the outer periphery of the container except for a small portion of the periphery) against the cover portion 3 of the container 1. The cover 3 of the container, in turn, is pressed against a planar portion of the device (not shown) positioned above the package 46 to seal all but the said unclamped portion of the periphery of the container against rupture. The porous membrane is situated atop or next to the unclamped portion of the periphery so that the extruded contents of the drug container pass through both the porous membrane and the unclamped portion of its periphery. This can be best visualized using FIG. 5. By this means, the mechanical action of the extrusion cam 22 upon the collapsible wall of the container expels the formulation from the container only through the portion of the periphery of the container that is not clamped against the cover by clamping member 47.

Rotation of the shaft 25 causes rotation of extrusion and clamping cams to be coordinated so that the clamping mechanism member 47 is held in place against the container cover portion during that portion of the rotational cycle of the cam shaft 25 that the extrusion cam 22 is approaching, holding, and beginning to diminish its maximum pressure against the collapsible wall of the container.

Figure 11:
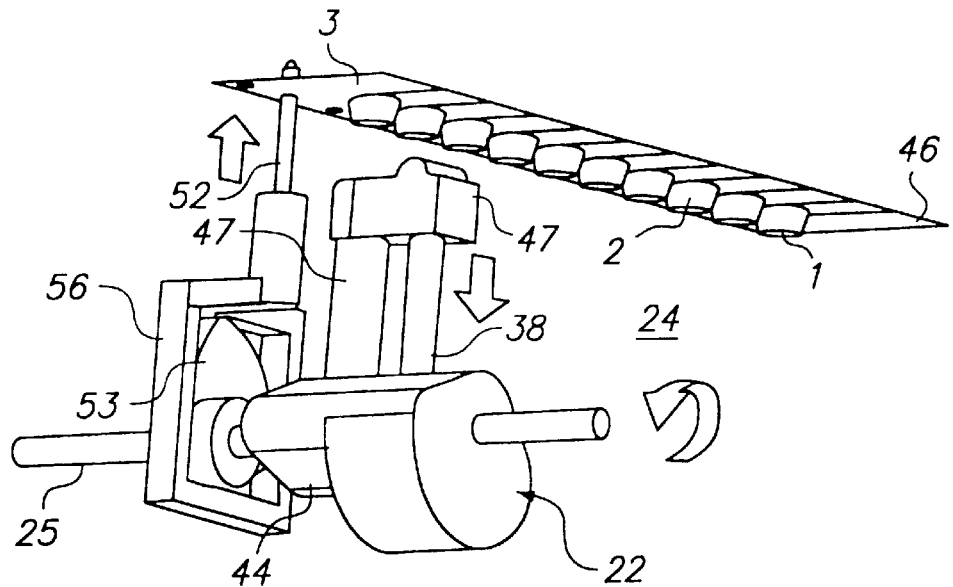
FIG. 11 is a schematic representation of the cam assembly wherein the advancement cam, the clamping cam and the extrusion cam are mounted on a single cam shaft with a claw engaging a package.
Figure 12:
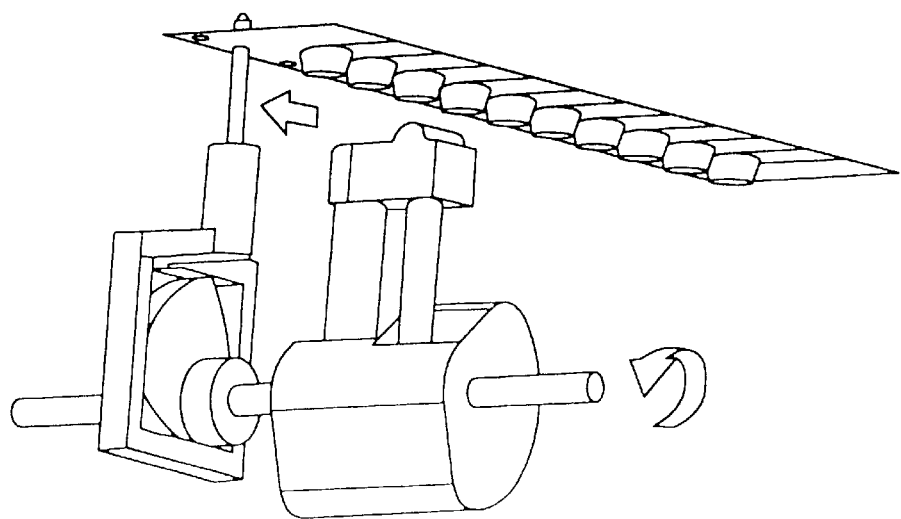
FIG. 12 is a schematic representation of the assembly of FIG. 11 showing the claw advancing the package.
Figure 13:
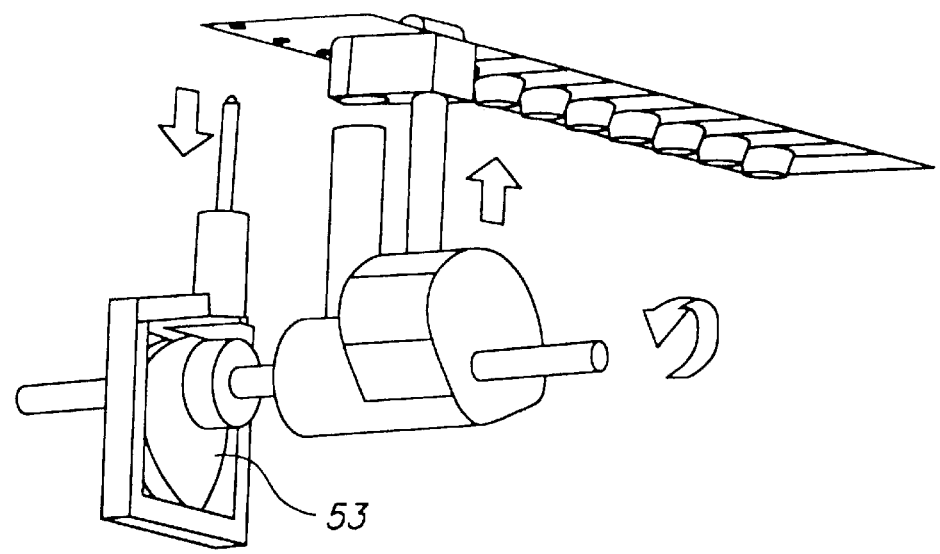
FIG. 13 is a schematic representation of the cam assembly of FIG. 11 showing the clamp assembly engaging a package and the claw disengaged.
Figure 14:
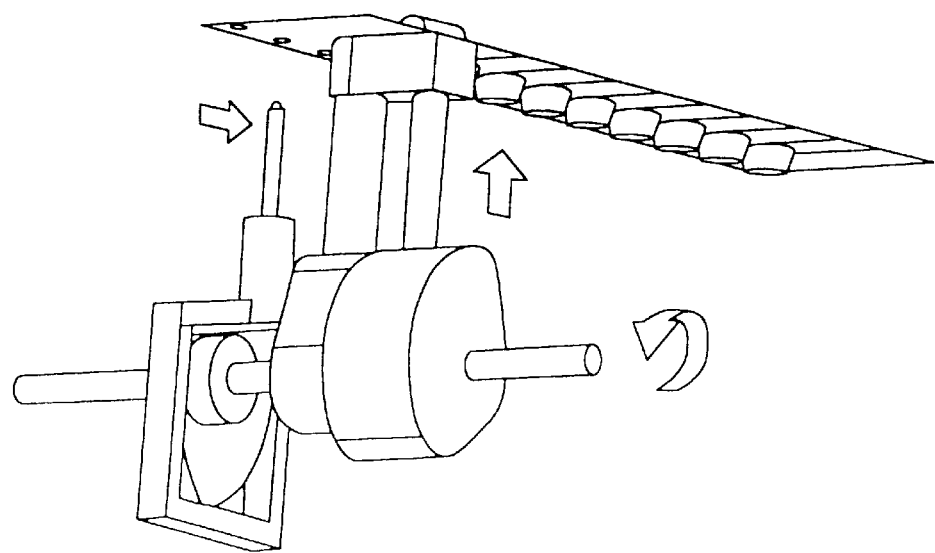
FIG. 14 is a schematic representation of the cam assembly of FIG. 11 showing the piston engaging a container of the package with the clamp engaged and the claw disengaged.
Figure 15:
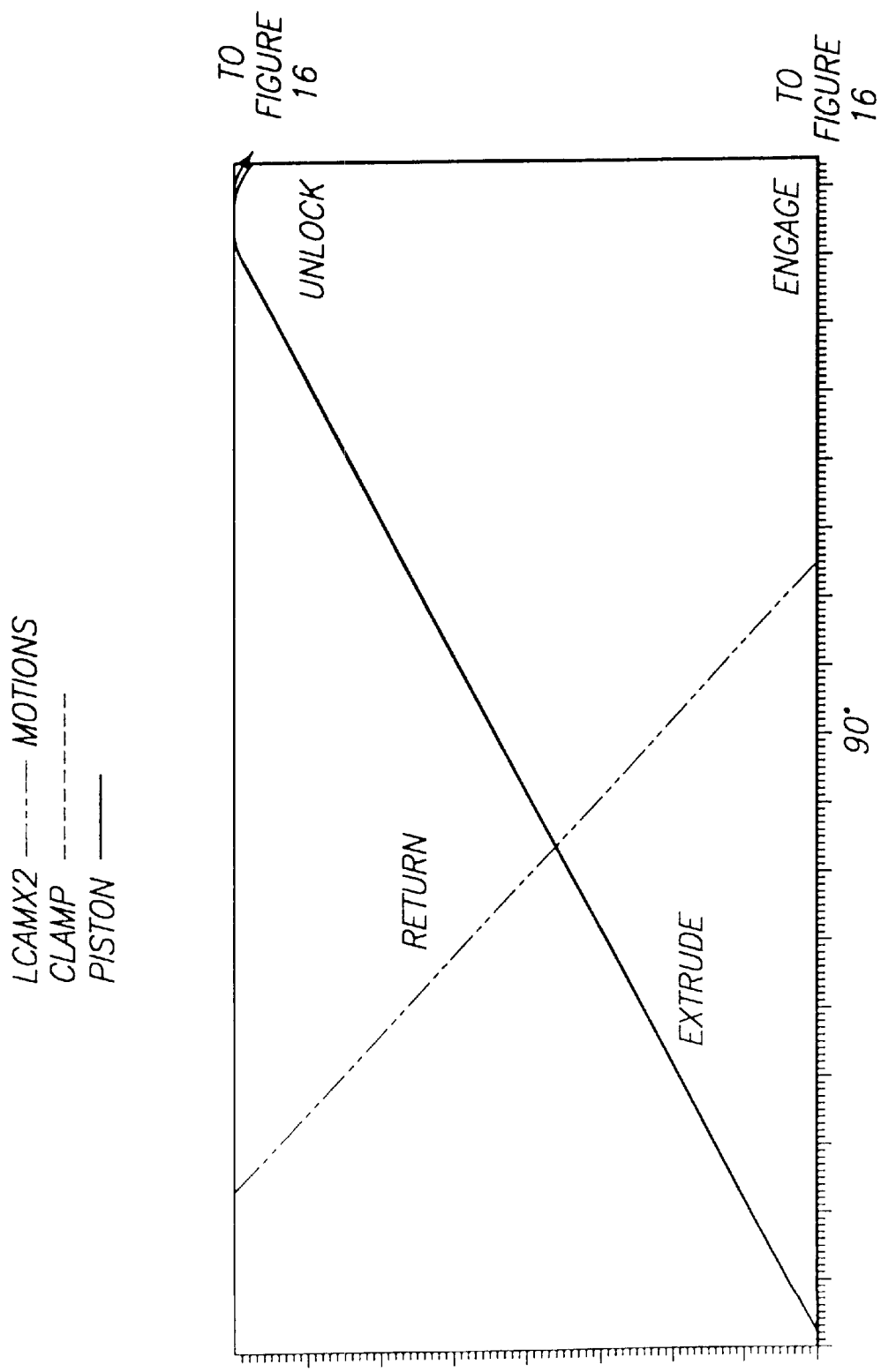
FIG. 15 shows a pressure phase diagram for 180° of a single rotation of the cam shaft in the cam assembly of FIG. 11 wherein the ordinate is a dimensionless representation of pressure applied from zero to maximum pressure and the abscissa is measured in the degrees of a circle.
Figure 16:
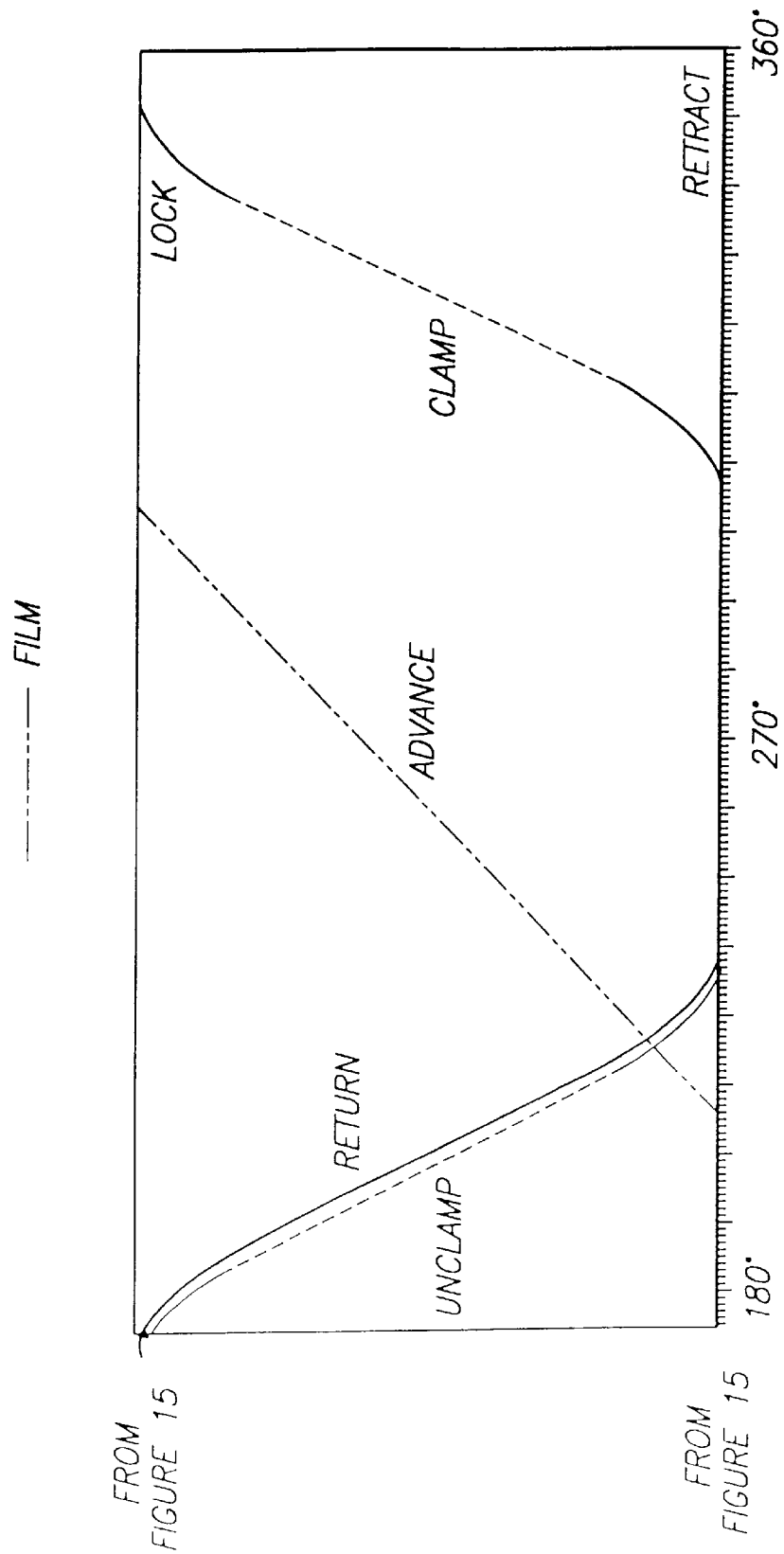
FIG. 16 shows a pressure diagram for the 180° of rotation following the 180° of rotation shown in FIG. 15 such that FIGS. 15 and 16 combine to show a 360° pressure phase diagram of a single rotation of the can shaft of the assembly of FIG. 11.

FIGS. 11, 12, 13 and 14 are placed in sequential order in accordance with how the cam assembly operates when the shaft 25 is turned. In FIG. 11 the claw 52 is engaging an opening in the package 46 and the clamping member 47 as well as the reciprocating piston 38 are in a down position. As the shaft 25 is turned the claw 52 removes the package 46 forward as shown in FIG. 12. As the shaft 25 continues to turn the claw 52 is lowered and the clamping member 47 is brought into position as shown in FIG. 13. When the clamping member 47 is securely holding the package in an aerosol position the piston 47 is moved upward to force the contents of a container 1 out of a porous membrane so that the formulation is aerosolized as shown in FIG. 14.

The purpose of the clamping cam 44 and clamping member 47 is to prevent rupture of the container at any point around its periphery, other than the unsealed portion, before, during, and after the period of time that a pressure is exerted against the collapsible wall. Therefore, the pressure exerted by the clamping member about the periphery of the collapsible wall must be sufficient to withstand the hydraulic pressure within the container caused by the piston 38.

To accomplish the purpose of preventing rupture of the container at any point except at the unclamped portion, the relative shapes of the extrusion and clamping cams are selected such that the clamping pressure is maximized while maximum extrusion pressure is applied and remains such for a longer period of the revolution of the cam shaft than is the maximum pressure of the extrusion cam. For example the clamping cam 44 has a relatively flat portion on its periphery for actuating and holding the clamping member 47 in place and that flat portion corresponds to a more sharply rounded portion of the periphery of the extrusion cam 22 that actuates the extrusion of the formulation.

As also shown in FIGS. 11–14, in the preferred embodiment the package 46 consists of a plurality of disposable drug containers 1 connected by an interconnecting member, for example in a linear array, such as a ribbon or tape 3. Alternatively, the package consists of a circular array of containers disposed at the periphery of the package, such as at the rim of a wheel. To automatically and sequentially move the drug containers into the drug release position for expulsion of the formulation, the cam assembly 24 preferably further includes an intermittent advancement mechanism, such as claw 52. The movement of the claw 52 as per FIG. 12 is actuated by an eccentric advancement cam 53 attached to the cam shaft 25 of the cam assembly. The advancement cam operates in a square dual axis space frame 56.

The eccentric cam 53 is placed within the substantially square frame 56 to restrict its translation to a square path dictated by the shape of the cam. The claw mechanism 52, which is mounted on the side of the frame 56 adjacent to the package, is driven by the eccentric cam 53 through a stroke with two dimensions of translation, which sequentially engages the package by means of a series of catches or claw receptacles thereon, such as a series of perforations or notches in the tape 3. The action of the claw 52 respectively (1) engages a catch or depression on the tape 3 of the package 46, (2) removes the emptied container 1 from the drug release position while advancing a loaded container into the position, (3) disengages the claw 52 from the catch, and (4) returns the claw 52 to the starting position by translation through a substantially square motion. The movement of the claw tip takes place in a plane at right angles to the driving spindle, the cam shaft 25.

As shown sequentially in FIGS. 11 through 14, with reference to a linear array of containers 1 in the package 46, rotation of the advancement cam 53 is timed with respect to the rotation of the extrusion cam 22, and the optional clamping cam 44, so that the claw 52 attached to square space frame 56 actuated by the advancement cam 53 engages a perforation on package 46 (FIG. 11) and advances a filled container 1 into the drug release position (FIG. 12) just before actuation of the clamping member 47 by the clamping cam 44. As the clamping mechanism moves into contact with the container, the claw disengages from the package (FIG. 13), and then the extrusion mechanism contacts the collapsible wall of the container while the claw returns to its home (disengaged) position (FIG. 14). The rotation of the advancement cam 53 is coordinated with those of the extrusion and clamping cams 22 and 44 so that the emptied container is removed from the drug release position upon release of pressure exerted thereon by piston 38 and clamping member 47, and a container 1 is advanced into the aerosol release position before the clamping 22 and extrusion 44 cams initiate a new pressure cycle. Although in FIG. 11 all three cams are shown mounted on a single cam shaft, it is also possible to utilize individual cam shafts to perform the above-described cam-driven operations.

In the most preferred embodiment (as shown in FIGS. 11–14) is adapted to utilize the combination of a package containing a number of disposable drug containers in a linear array, and a cam assembly that includes all three cams mounted on a single cam shaft. The preferred timing of the rotation of the cams on the cam shaft is shown in FIGS. 15 and 16. During any cycle of rotation of the cam shaft the extrusion cam progressively increases pressure against the collapsible wall of the container via the piston 38 from zero to the maximum amount during any phase of rotation of the cam shaft from 0° to 170°, and progressively decreases pressure from the maximum pressure to zero during the phase of rotation from about 170° to 230°. At the same time the reciprocating clamping cam progressively presses the clamping member against the cover of the container during the phase of rotation of the cam shaft from about 295° to 355°, holds the clamping member against the periphery of the collapsible wall during the phase of rotation from about 0° to 170° of the following cycle of rotation, and progressively releases its pressure during the phase of rotation from about 170° to 230° of rotation.

As is well known to those of skill in the art, the radii of the circular arcs that describe the eccentric cam can be of any convenient relative lengths to accomplish the above described movement, with eccentric cams generally consisting of two concentric arcs of circles with radii $r_1$ and $r_2$ joined by two other arcs of circles with radii $r_1+r_2$ The stroke of the claw is governed by the difference in the two radii $(r_1-r_2)$. The advancement phase of the square motion of the claw is preferably about ¼ of the complete phase cycle of the cam shaft and, hence, of the advancement cam. Thus, one skilled in the art will appreciate that variations of the various phases of the cam cycle and the movements of the individual cams are contemplated within the scope of this invention within the above general parameters.

Alternatively, the device utilizes a rigid multidose container containing bulk drug, and the porous membranes and low resistance filters are contained in tapes or ribbons as shown in FIGS. 7 or 8. In this embodiment of the invention the cam assembly contains the above described eccentric advancement cam and claw for removing an emptied container and advancing a loaded container into place, but does not utilize the extrusion and clamping cams. Timing of the rotation of the advancement cam is such that the advancement mechanism removes a used porous membrane, low resistance filter, or both, after each release of drug from the multidose container by operation of the drug administration device and advances fresh ones into place for the next operation.

The motor, and consequently the cam assembly, can be manually actuated or actuated automatically by a signal received from a microprocessor which receives information from sensors regarding inspiratory flow and volume.

In addition, the device preferably includes monitoring and electronic components. For example, the device preferably includes a means for recording a characterization of the inspiratory flow profile as well as the total lung capacity possible for the patient by including a microprocessor 26 (FIG. 9) in combination with a read/write memory means and a flow measurement transducer. By using such devices, it is possible to change the firing threshold as well as the volume of aerosolized and/or unaerosolized air released at any time in response to an analysis of the patient's inspiratory flow profile, total lung volume, and area of the lung to be treated. It is also possible to record drug dosing events over time. In a particularly preferred embodiment the characterization of the inspiratory flow can be recorded onto a recording means on the disposable package.

The drug delivery device of the invention is preferably designed to include visual signals which prompt the patient to inhale at a preferred rate. For example, the device is designed with a sensor which senses inspiratory flow rate and sends the sensed information to a microprocessor, which is connected to a light diode or series of diodes. When a patient inhales too slowly the diodes do not light. When a patient inhales too rapidly, the diodes will emit a flashing red signal, indicating to the patient that the rate of inhalation should be decreased. When the patient inhales at the desired inspiratory flow rate, a light on the device will emit a constant green signal. The desired flow rate is in the range of about 0.10 to about 2.0 liters per second, preferably 0.2 to about 1.8 liters per second, and more preferably 0.15 to 1.7 liters per second.

It is important to note that a variety of devices can be used in order to carry out the methodology (including the respiratory disease treatment methodology) of the present invention. However, the device must be capable of aerosolizing drug formulation in a container, and preferably by forcing formulation through a low resistance filter and a porous membrane with the release point based on pre-programmed criteria, which may be mechanically set or electronically set via criteria readable by the microprocessor 26. Further, the device must be capable of releasing specific volumes of aerosolized and unaerosolized air based on total lung volume and the area of the lung to be treated. The details of the microprocessor 26 and the details of other drug delivery devices which include a microprocessor and pressure transducer of the type used in connection with the present invention are described and disclosed within U.S. Pat. No. 5,404,871, issued Apr. 11, 1995, entitled "Delivery of Aerosol Medications for Inspiration," which patent is incorporated in its entirety herein by reference, and it is specifically incorporated in order to describe and disclose the microprocessor and program technology used therewith.

The pre-programmed information is contained within a nonvolatile memory that can be modified via an external device. The memory is programmed with information specific to the patient, such as the total lung capacity, which information determines volumes of air released based on the target area of the lung. In another embodiment, this pre-programmed information is contained within a "read only" memory which can be unplugged from the device and replaced with another memory unit containing different programming information. In yet another embodiment, microprocessor 26, containing "read only" memory that in turn contains the pre-programmed information, is plugged into the device. For each of these three embodiments, when the programming of the memory device readable by the microprocessor 26, the behavior of the device is radically changed, by causing microprocessor 26 to be programmed in a different manner, e.g., to release different volumes to treat different areas of the lung. The programming can also accommodate different drugs and different types of treatment.

As shown in FIG. 9, microprocessor 26 sends signals via electrical connection 27 to electrical actuation device, such as motor 28, which actuates the cam shaft 25 for actuating the cam 22. Cam 22 contacts and applies pressure to the collapsible wall 2, thus forcing drug formulation in a container 1 to pass through a low resistance filter 301 and a porous membrane 302 and to be aerosolized so that an amount of aerosolized drug is delivered into the inspiratory flow path 29 when the flexible membrane 302 protrudes outward through the flow boundary layer. A signal may also be sent to a heater 14 to add heat energy to the air in the flow path 29. The device 28 can be a solenoid, motor, or any device for converting electrical to mechanical energy. Further, microprocessor 26 keeps a record of all drug dosing times and amounts, using a read/write non-volatile memory, which is in turn readable by an external device. Alternatively, the device records the information onto an electronic or magnetic strip on the package 46. The recorded information can be read later by the care-giver to determine the effectiveness of the treatment. In order to allow for ease of use, it is possible to surround the inspiratory flow path 29 with a mouth piece The electrical actuation means 28 is in electrical connection with the flow sensor 31, which sensor is capable of measuring a flow rate of about 0 to about 800 liters per minute. It should be noted that inhalation flow rates are less than exhalation rates. For example the maximum inhalation rate is about 200 lpm, and the maximum exhalation rate is about 800 lpm. A variety of different types of flow sensors may be used as per U.S. Pat. No. 5,394,866, issued Mar. 7, 1995, U.S. Pat. No. 5,404,871, issued Apr. 11, 1995 and U.S. Pat. No. 5,450,336, issued Sep. 12, 1995, which are incorporated herein by reference. As shown in FIG. 9, the flow sensor 31 includes screens 32, 33 and 34 which are positioned approximately ¼" apart from each other, but may be comprised of a single screen, or include a non-linear flow path. It is preferable to include the desiccator 41 at a point prior to the screens 32, 33 and 34 in the flow path so that the elimination of water vapor is considered in any measurement.

Tubes 35 and 36 open to the area between the screens 32, 33 and 34 with the tubes 35 and 36 being connected to a conventional differential pressure transducer 37. Another transducer designed to measure outflow through the opening 38 is also preferably included or the flow sensor 31 is designed so that the same components can measure inflow and outflow. When the user draws air through inspiratory flow path 29, air is passed through the screens 32, 33 and 34 and the air flow can be measured by the differential air pressure transducer 37. Alternatively, other means to measure pressure differential related to air flow, such as a conventional measuring device in the air way, may be used. The flow sensor 31 is in connection with the electrical actuation means or motor 28 (via the connector 39 to the processor 26), and when a threshold value of air flow is reached (as determined by the processor 26), the electrical actuation means or motor 28 actuates the mechanical means (levers, gears, etc.) 23 to rotate the cam 22 which contacts and applies force to collapsible wall 2 to force the release of formulation from a container 1 so that a controlled amount of formulation is delivered to a specific volume of air which is aerosolized thereby and delivered to the patient. The microprocessor 26 is optionally connected to an optionally present vibrating device 45 which may be activated.

In order to target an area of the lung particle size can be adjusted by adjusting the size of the pores in the porous membrane through which the formulation is moved to create an aerosol. If necessary, heat can be added (e.g., using the air-heating mechanism 14 as described above) to evaporate liquid carrier away from aerosolized particles formed. Particle size adjustment is combined with adjustments in the volume of aerosolized and non-aerosolized air released to target a particular area of the lung. Thus, the device preferably includes some mechanism for completely shutting off inhalation to the patient. This mechanism can be an all or nothing mechanism meaning that the flow can be completely free or shut off completely. However, in one embodiment the mechanism provides for a variable flow restriction so that the flow can be completely free to infinitely small. The device may be a ball valve, needle valve or more preferably a gate valve which is closed by the use of a motor or solenoid actuator. Preferably, the mechanism is designed such that it can be moved from a fully opened to a fully closed position in less than 100 milliseconds and preferably in less than 10 milliseconds.

To use the device 40 a patient (see FIG. 9 inhales air from the mouthpiece 30. The air drawn in through the opening 38 (and optionally the desiccator 41) flows through the flow path 29 of the channel 11. The disposable package 46 is comprised of a plurality of disposable containers 1. Each container 1 includes a drug formulation 5 and is covered by the porous membrane 302. Where desired, an air-heating mechanism 14 may be located in the flow path 29, and is preferably positioned such that all or only a portion of the air flowing through the path 29 will pass by the heater, e.g., flow vent flaps can direct any desired portion of air through the heater 14. The heat is preferably turned on for 30 sec or less prior to inhalation and turned off after drug delivery to conserve power.

EVAPORATION AFTER AEROSOLIZATION

In another embodiment the formulation is heated using an optional air-heating mechanism 14 that heats the surrounding air within the flow path 29 (FIG. 9). The formulation is heated after it has been forced through the pores of the low resistance filter 301 and the porous membrane 302 and aerosolized i.e., energy is preferably added by heating the surrounding air by means of the air-heating mechanism 14 positioned anywhere within the flow path 29 with the heater positioned after the porous membrane (FIG. 9). If desired, sufficient heat can be added such that the only material reaching the patient is the substantially dry powder drug.

Heating mechanisms of various types can be used. For example, see the heating mechanism in the self-contained, portable sealer for plastic colostomy bags in French patent 2,673,142 which is incorporated herein by reference. A portable heater is also taught in European patent applications 0,430,566 A2 for a "Flavor delivering article" and 0,358,002 for "Smoking articles utilizing electric energy," both of which are incorporated herein by reference to disclose and describe heating components powered by batteries.

The amount of energy added by the formulation vibrating device 45 or air-heating mechanism 14 is controlled by the microprocessor 26 based on the amount of formulation in the container 1 and other factors such as the concentration of the drug and surrounding humidity. A hygrometer 50 and thermometer 51 are electrically connected to the microprocessor 26 allowing the amount of heat to be added to be adjusted based on ambient humidity and temperature.

Potent drugs and/or diagnostics that are highly soluble in water, ethanol and/or mixtures thereof are particularly useful in that such compounds can be used in small amounts in high concentration and thus require less energy to obtain evaporation of the carrier. Particles having a diameter of 6.3 microns can be formed and subjected to evaporation to obtain a particle of one micron in diameter. In the respiratory track this one micron particle would be expected to grow to a 3 micron particle due to moisture added from the high humidity environment of the respiratory tract.

Information in US95/12744 can be used to calculate the amount of preheating needed to evaporate all or substantially all of the carrier in the aerosolized particles. As an example, assume the initial ambient conditions are 25° C. and 50% relative humidity. Further, assume that one wants to evaporate 10 $\mu$l (10 mgs) of water from an aqueous drug solution. Finally, assume the final relative humidity is 75%. Under these conditions the aqueous carrier would not evaporate completely. More specifically, the final particles would contain approximately equal amounts of drug and water. To calculate the amount of energy to add for this delivery maneuver, refer to the graph of US95/12744. Locate the point corresponding to 25° C. and 50% relative humidity. Move up by 10 milligrams, the amount of water to be evaporated. Now move to the left until the 75% RH curve is crossed. This occurs at about 29° C. These conditions (75% RH and 29° C.) represent the condition of the air as delivered to the patient. However, still more energy must be added to make up for the cooling of the air as the water evaporates. To calculate this amount of heat, move parallel to the air mass trajectory curves (downward and to the right) until the initial ambient water vapor density is reached, at approximately 47° C. Thus, sufficient heat to warm the air by 22° C. must be added to achieve near complete evaporation. A graph of US95/12744 includes similar information with respect to ethanol which can be used in a similar manner.

The amount of energy required for the heating devices 14 can be reduced by including in the device a desiccator 41. The desiccator 41 is preferably located at the initial opening 38 but may be located elsewhere in the flow path 29 prior to a point in the flow path when the formulation is fired into the flow path. The desiccator material can be any compound which absorbs water vapor from air. For example, it may be a compound selected from the group consisting of $P_2O_5$, $Mg(ClO_4)$, $KOH$, $H_2SO_4$, $NaOH$, $CaO$, $CaCl_2$, $ZnCl_2$, and $CaSO_4$.

The evaporation and growth rates of aqueous particles is a function of their initial diameter, the amount of drug dissolved therein (concentration) and the ambient relative humidity. The determining factor is whether the water vapor concentration at the surface of the particle is higher or lower than that of the surrounding air. Because the relative humidity at the surface of a particle (i.e. particle of aerosolized formulation) is close to 100% for all the high concentration formulations, a five micron particle will evaporate to a 1 micron dry particle in 0% humidity in less than 20 ms. However, if a particle of drug 1 micron diameter is inhaled into the lungs (99.5% humidity) it will grow to about 3 microns in diameter in approximately one second by accumulating water from the humid lung environment. At an appropriate point in the inspiratory cycle, the microprocessor can send a signal to send power from the power source 43 to the air-heating mechanism 14 which uses information from the hygrometer 50, thermometer 51 and particle size and amount of formulation.

PREFERRED FLOW RATES/VOLUMES

U.S. Pat. No. 5,509,404, issued Apr. 23, 1996 shows two-dimensional graphs wherein the inspiratory flow rate is plotted against the inspiratory volume. The patient's inspiratory flow rate and inspiratory volume are simultaneously and separately measured. The measurement is taken and the information obtained provided to a microprocessor which is programmed to release drug: (1) at the same point relative to inspiratory flow and inspiratory volume at each release of drug and (2) to select that point within prescribed parameters of inspiratory flow rates and inspiratory volumes. The data in the graphs of U.S. Pat. No. 5,509,404 were obtained by programming the microprocessor to release a radioactively-labeled drug to a human in four general areas with respect to the inspiratory flow rate and inspiratory volume parameters (labeled A, B, C and D). In area A (showing solid triangles), the drug was released when the patient's inspiratory flow rate was "slow to medium" (0.10 to 2.0 liters per sec) with an "early" inspiratory volume of 0.15 to 0.8 liters. In area B (showing open triangles), the drug was released at a "slow" inspiratory rate/0.10 to 1.0 liters/sec) and a "late" volume (1.6 to 2.8 liters). In area C (showing solid diamonds), the drug was released at a "fast" inspiratory flow rate (3.5 to 4.5 liters/sec) and a "late" volume. In area D (showing solid circles), the drug was released at a "fast" inspiratory flow rate and an "early" inspiratory volume.

Data demonstrated that it is important to simultaneously and separately consider (in real time) both inspiratory flow rate and inspiratory volume when determining the point for drug release for intrapulmonary drug delivery. If both measurements are separately considered the drug can be released anywhere along the abscissa and ordinate scales. Once a point is selected, that selected point is used again and again by a given patient to obtain repeatable dosing. The same point should be selected each time as closely as possible and within a margin of errors of ±10% with respect to each criteria. The margin for error can be increased and still maintain acceptable levels of repeatable dosing, but the error should keep the drug release point inside a predetermined area. Thus, when treating a patient the drug should be released at approximately (±10%, preferably ±5% and most preferably as close as possible to the first release point) the same inspiratory flow rate and inspiratory volume each time—going back to the same point each time for the same patient ensures repeatable dosing. In practice, the tighter the point is defined the greater the repeatability of dosing. However, if the point is defined too precisely it can be difficult for the patient to obtain that rate/volume point again. Thus, some degree of tolerance is generally applied.

In addition, it was found that within particular ranges with respect to inspiratory flow rate and inspiratory volume it was possible to obtain a consistently high percentage amount of drug deposited in the lung. Some areas clearly showed the highest percentage of drug delivered to the patient based on the amount of drug released. Using this information it was possible to calculate a specific area regarding inspiratory flow rate and inspiratory volume at which it is possible to obtain not only a high degree of repeatability in dosing, but obtain a higher percentage of drug being delivered based on the percentage of drug released. Specifically, it was determined that the drug should be released within an inspiratory flow rate range of 0.10 to 2.0 liters per second and at an inspiratory volume in the range of about 0.15 to about 0.80 liters.

By examining delivery of drug associated with the data points plotted, it is possible to determine a preferred and particularly preferred and most preferred range. The preferred range shows drug released at a volume of 0.15 to 0.8 liters and rate of 0.10 to 2.0 liters/second. The particularly preferred range plotted indicates that the inspiratory flow should be within the range of 0.2 to about 1.8 liters per second with an inspiratory volume in the range of 0.15 to about 0.4 liters. The most preferred range is from about 0.15 to about 1.8 liters per second for the inspiratory flow rate and about 0.15 to about 0.25 liters for the inspiratory volume. Thus, preferred delivery can be obtained by:

(1) repeatedly delivering aerosolized formulation to a patient at the same simultaneously and separately measured inspiratory flow rate and inspiratory volume and
(2) releasing aerosol to the patient within specified therapeutically effective ranges. The invention involves releasing aerosol (after measuring) inside the ranges.

Thus, the release could begin inside or outside the range. Preferably the aerosol release begins inside the range and more preferable begins and ends inside the ranges.

VELOCITY

The velocity at which the aerosol is released to the patient may also be important to obtain a high degree of repeatability in dosing and providing for a high percentage of aerosol particle being delivered to the patient's lungs. Most preferably, the aerosol is released from a container in a direction which is normal to the patient's airflow. Accordingly, the aerosol may be released directly upward so that its flow is at a 90° angle with respect to the patient's inspiratory flow which is directly horizontal. After being released, the aerosol velocity decreases and the aerosol particles remain suspended for a sufficient period of time to allow the patient's inspiration to draw the aerosol into the patient's lungs. The velocity of aerosol released in the direction from the aerosol release point to the patient may match the patient's inspiratory flow rate but is preferably slower that the patient's inspiratory flow rate and is most preferably about zero. The velocity may be slightly negative, i.e., in a direction away from the patient. The velocity may range from −2.0 liters/sec to 2.0 liters/sec and is preferably zero. It is not desirable to project the aerosol toward the patient at a rate above the speed of the patient's breath as such may result in particles being deposited on the back of the patient's throat. Thus, the aerosol release speed should be equal to or less than the breath speed. The actual speed of release can vary depending on factors such as the particle size, the particle composition and the distance between the point of release and the patient. The velocity is preferably such that the particles will (due to air resistance) slow to zero velocity after traveling a distance of about 2 centimeters or less. In general, the shorter the distance required to slow the particles to zero velocity the better.

PARTICLE SIZE ADJUSTMENT

One aspect of the invention involves manipulating the particle sizes in order to treat particular areas of the lung. For example, when it is desirable to treat the outer most peripheral areas of the lung the method of the present invention involves reducing the particle size to a particle size in the range of 0.5 to 3 microns. When it is desirable to treat the more central areas of the lung larger particle sizes are used and the particle size is adjusted to a size in the range of 5 to 9 microns. In some instances it is desirable to treat both areas simultaneously and to deliver aerosolized drug wherein the particle size is distributed over two different ranges. For example, the particle size could be distributed closely to a size of about 2 microns (within the range of 0.5 to 3 microns) for one group of particles and distributed close to a particle size of about 7 microns (within the range of 5 to 9 microns). The smaller particles would reach and treat, primarily, the peripheral areas of the lungs whereas the larger particles would reach and primarily treat the central areas of the lungs. In some instances, the particle size distribution is kept relatively broad over a range of 0.5 to 9 microns.

Aerosol particle size can be adjusted by adjusting the size of the pores of the membrane. In general, the aerosol is created by forcing the formulation through a porous membrane having pores in the range of about 0.25 to 6.0 microns in size, preferably 1.0 to 5.0 microns and more preferably 1.5 to 3.0 microns. When the pores have this size the particles which escape through the pores to create the aerosol will have a diameter about twice the diameter of the pore size. In order to ensure that the low resistance filter has the same or less flow resistance as the porous membrane, the pore size and pore density of the filter should be adjusted as necessary with adjustments in pore size and pore density of the porous membrane.

Particle size can also be adjusted by adding heat to evaporate carrier. From the period of time from the formation of the aerosolized particles until the particles actually contact the lung surface, the size of the particles is subject to change due to increases or decrease in the amount of water in the formulation due to the relative humidity within the surrounding atmosphere. More specifically, water vapor present in the surrounding atmosphere contacts the particles which absorb the water and grow in size. Alternatively, in a particularly dry atmosphere, water is drawn away from the particles and they are reduced in size. In order to obtain consistency in terms of the size of particles delivered to the patient regardless of the surrounding atmosphere, it may be desirable to include a component within the drug delivery device which adds energy to the surrounding atmosphere (heats the atmosphere) and thereby minimizes the effect of high humidity conditions and reduces the particle size to a minimum consistent size. Alternatively, water vapor may be added to the surrounding atmosphere of the aerosol so that the particles would always enlarge to a maximum consistent size. Detailed information on dynamic particle size adjustment is contained within U.S. patent application entitled "Dynamic Particle Size Reduction for Aerosolized Drug Delivery", U.S. Pat. No. 5,522,385, issued Jun. 6, 1996, which is incorporated herein by reference in its entirety and specifically incorporated in order to disclose and describe components used in particle size adjustment by the addition of heat to air surrounding the particles.

Particle size may also be adjusted by the use of a vibration device which provides a vibration frequency in the range of about 800 to about 4000 kilohertz.

VIBRATION DEVICE

The vibration device 45 creates ultrasonic vibrations which are preferably at right angles to the lane of the membrane 302. The device 45 may be in the form of a piezoelectric ceramic crystal or other suitable vibration mechanism. A vibrating device 45 in the form of a piezoelectric crystal may be connected to the porous membrane by means of an attenuator horn or acoustic conduction mechanism, which when correctly matched with the piezoelectric crystal frequency, efficiently transmits ultrasonic oscillations of the piezoelectric crystal to the resonance cavity and the porous polycarbonate membrane and if sized correctly permits the ultrasonic energy to be focused in a polycarbonate membrane 302 allowing for maximum use of the energy towards aerosolizing the liquid formulation 5. The size and shape of the attenuator horn is not of particular importance. It is preferred to maintain a relatively small size in that the device is hand held. The components are chosen based on the particular material used as the porous material, the particular formulation used and with consideration of the velocity of ultrasonic waves through the membrane to achieve a harmonic relationship at the frequency being used.

A high frequency signal generator drives the piezoelectric crystal. This generator is capable of producing a signal having a frequency of from about 575 kilohertz (Khz) to about 32,000 kilohertz. The power output required depends upon the amount of liquid being nebulized per unit of time and the area and porosity of the membrane (generally comprised of a polymeric plastic-like material) used for producing the drug dosage unit and/or the efficiency of the connection.

Vibration is applied while the formulation 5 is being forced from the pores of the polycarbonate membrane 302. The formulation can be aerosolized with only vibration i.e., without applying pressure. Alternatively, when vibration is applied in certain conditions the pressure required for forcing the liquid out can be varied depending on the liquid, the size of the pores and the shape of the pores but is generally in the range of less than 50 bar, preferably less than 35 bar and may be achieved by using a roller, bellows, a blast of forced compressed gas, or other suitable device. The vibration frequency used and the pressure applied can be varied depending on the viscosity of the liquid being forced out and the diameter and length of the openings or pores.

It is desirable to force formulation through the low resistance filter and the porous membrane with a relatively low pressure e.g., pressure less than 50 bar, preferably pressure less than 35 bar in that lower pressure reduces the chance of breaking the membrane during the release of formulation and makes it possible to make a thinner membrane. The thinner membranes make it easier to make small holes in that the holes or pores of the membrane are created using a focused LASER. It is possible to reduce the pressure further by making the holes conical in cross-section. A LASER with a conical focus is used to burn holes through the membrane. The larger diameter of the conical shape is positioned next to the formulation and the smaller diameter opening is the opening through which the formulation ultimately flows. The ratio of the smaller opening to the diameter of the larger opening is in the range of about 1:2 to about 1:20 i.e., the larger opening is between 2 and 20 times the diameter of the smaller opening. By creating conical openings wherein the smaller end of the cone has a diameter of less than 6 microns it is possible to produce particles which have a diameter of less than 12 microns and it is also possible to force the formulation through the pores using a pressure of less than 500 psi. The small end of the conical opening preferably has a diameter of less than 3 microns for systemic delivery and less than 5 microns for pulmonary delivery and the pressure used for forcing formulation through the pores is preferably less than 350 psi.

When small aerosolized particles are forced into the air, the particles encounter substantial frictional resistance. This may cause particles to slow down more quickly than desired and may result in particles colliding into each other and combining, which is undesirable with respect to maintaining the preferred particle size distribution within the aerosol. In order to aid in avoiding the particle collision problem, it is possible to include a means by which air flow and the flexible membrane 302 prevent collisions. Specifically, the patient inhales thereby creating an air flow toward the patient over the protruding membrane 302. The air flow carries the formed particles along and aids in preventing their collision with each other. The shape of the container opening, the shape of the membrane covering that opening, as well as the positioning and angling of the flow of air through the channel 11 relative to the direction of formulation exiting the pores of the membrane 302 can be designed to aid in preventing particle collision. It is desirable to shape the opening and matching membrane so as to minimize the distance between any edge of the opening and the center of the opening. Accordingly, it is not desirable to form a circular opening which would maximize the distance between the outer edges of the circle and the center of the circle, whereas it is desirable to form an elongated narrow rectangular opening covered by a rigid convex membrane 302 as shown in FIG. 5. Using such a configuration makes it possible to better utilize the air flow relative to all of the particles of formulation being forced form the pores of the membrane 302. When a circular opening is used, particles which are towards the center of the circle may not be carried along by the air being drawn over the membrane 302 and will collide with each other. The elongated rectangle could be formed in a circle, thereby providing an annular opening and air could be forced outward from the outer and inner edges of the circle formed.

Those skilled in the art will recognize that some adjustments can be made in the parameters such as the size of the pores from which drug is released, vibration frequency, pressure, and other parameters based on the density and viscosity of the formulation keeping in mind that the object is to provide aerosolized particles having a desired diameter.

FIRING POINT

It is important to note that the firing threshold of the device is preferably not based on a single criterion such as the rate of air flow through the device or a specific time after the patient begins inhalation. The firing threshold is based on an analysis of the patient's total lung capacity and inspiratory flow profile. This means that the microprocessor controlling the device takes into consideration the instantaneous (1) air flow rate, (2) the cumulative inspiratory flow volume, and (3) the volume of aerosolized and/or unaerosolized air being released. All three factors are simultaneously considered in order to determine the optimal point in the patient's inspiratory cycle most preferable in terms of (1) directing medication to a target area of the lung, (2) reproducibly delivering the same amount of drug to the patient with each release of drug, and (3) efficiently delivering drug to the lung.

METHOD OF ADMINISTRATION AND OPERATION OF THE DEVICE 40

The method and device of the invention provides a number of features which make it possible to achieve the controlled and repeatable dosing to particular target areas of the lung required for treatment. First, total lung capacity is determined and the information used to determine the volume of aerosolized and unaerosolized air to be released. Second, the low resistance filter prevents undissolved drug particles from reaching the porous membrane and being delivered to the patient. Third, the membrane is permanently convex or is flexible and protrudes into fast moving air aiding the elimination of particle collisions. Fourth, it is possible to eliminate any carrier from the aerosolized particles and provide dry drug particles to a patient which particles can be manufactured to have a uniform size. By delivering particles of a desired uniform size, both the targeting and repeatability of dosing is enhanced regardless of the surrounding environment, e.g., different humidity conditions. Fifth, the device makes it possible to administer aerosol at the same point with respect to inspiratory flow rate and inspiratory volume at each delivery point thereby improving repeatability of dosing.

The method of the invention may involve the release of aerosol and particle free air. The drug or diagnostic in the aerosolized air is preferably derived from a liquid, flowable formulation in individual disposable containers which may be interconnected in a package. This is desirable in that the liquid, flowable formulation is packaged under a sterile environment and therefore does not require and preferably does not include additional materials such as antifungal, bacteriostatics, and preservatives which would normally be required in a liquid formulation if the formulation was to be opened, exposed to air, closed and later used again. In a preferred embodiment a new container and membrane are used for each release of aerosol (see FIG. 9). Thus, the membrane and container are disposable thereby preventing clogging of pores which takes place with reuse. In another embodiment (see FIG. 7) the container of formulation includes multiple doses but a new membrane is used for each release of aerosol.

In addition, the present invention offers advantages due to the relatively slow speed at which the aerosol dispersion is delivered to the patient. a conventional metered dose inhaler device discharges the aerosol outward at a relatively high rate of speed which causes a large amount of the aerosol particles to make contact with the inside of the patient's mouth and the back of the patient's throat. This decreases the amount of formulation actually administered to the patient's lungs as compared with the present system, wherein the aerosol is delivered at a relatively slow rate of speed and can be inhaled slowly by the patient.

In general, the method preferably uses a delivery device which is not directly actuated by the patient in the sense that no button is pushed nor valve released by the patient applying physical pressure. On the contrary, the device of the invention provides that the actuation mechanism which causes formulation to be forced from a container automatically upon receipt of a signal from a microprocessor programmed to send a signal based upon data received from a monitoring device such as an airflow rate monitoring device. A patient using the device withdraws air from a mouthpiece and the inspiratory rate, and calculated inspiratory volume of the patient is measured simultaneously one or more times in a monitoring event which determines an optimal point in an inhalation cycle for the release of a dose of any desired drug. Inspiratory flow and total lung capacity are preferably measured and recorded in one or more monitoring events for a given patient in order to develop an inspiratory flow profile for the patient. Recorded information is preferably analyzed by the microprocessor in order to deduce a preferred point within the patient's inspiratory cycle for the release of an aerosolized volume of air with the preferred point being calculated based on the most likely point to result in delivery to the target area of the lung.

A monitoring device continually sends information to the microprocessor, and when the microprocessor determines that the optimal point in the respiratory cycle is reached, the microprocessor actuates a component which fires a mechanical means (and activates the vibration device) which causes formulation to be forced out of the container and aerosolized. The signal preferably also opens a valve (if not already open) to allow release of a specific volume of aerosolized air. Accordingly, an aerosolized volume of air is delivered at a pre-programmed place in the inspiratory flow profile of the particular patient which is selected specifically to target a given area of the lung. It is pointed out that the device of the present invention can be used to, and actually does, improve the efficiency and repeatability of delivery.

Another feature is the release of a tightly controlled volume of aerosolized air (with a narrow range of particle size) to assure the delivery to a particular target area of the lungs of each individual patient. The low resistance filter, porous membrane and, optionally, the heating component(s) and/or the desiccator to remove water vapors aid in providing improved targeting and repeatability in dosing in that the particles reaching the patient will have the same composition (i.e., will not contain undissolved drug or diagnostic particles) and size (designed for a target area of the lung). By keeping the particle composition and size the same at each dosing event the particles deposit at the same general area of the lung at each event. Because the aerosol release mechanism is fired automatically and not manually, it can be predictably and repeatedly fired at that same point in the inspiratory cycle Because dosing events are preferably preceded by monitoring events, the volume of aerosolized and unaerosolized air released and the point in the inspiratory cycle of the release can be readjusted based on the particular condition of the patient.

The device of FIG. 9 shows all of the components present within the single, hand-held, portable breath actuated device, e.g. the microprocessor 26 and flow sensor 31 used to provide the electronic breath actuated release of specific volumes of aerosolized and unaerosolized air. The device of FIG. 9 includes a holding means and mechanical means and preferably operates electronically, i.e., the actuation means is preferably not directly released by the user. The patient inhales through inspiratory flow path 29 which can form a mouth piece 30. Air enters the device via the opening 38.

The inhaling is carried out in order to obtain a metering event using the differential pressure transducer 37. Further, when the inspiratory flow meets a threshold of a pre-programmed criteria, the microprocessor 26 sends a signal to an actuator release electrical mechanism 28 which actuates the mechanical means 23, a cam 22 or equivalent thereof, thereby forcing aerosolized formulation into the channel 11, and out of the membrane 302 into the flow path 29 where the air surrounding the particles is optionally heated by the air heater 14. Further details regarding microprocessors 26 of FIG. 9 are described within U.S. Pat. No. 5,394,866, issued Mar. 7, 1995, entitled "An Automatic Aerosol Medication Delivery System and Methods", and U.S. Pat. No. 5,608,647, issued Mar. 4, 1997, incorporated herein by reference in their entirety and specifically incorporated in order to describe and disclose flow measurements, the microprocessor and program technology used therewith. The volume of aerosolized and unaerosolized air is determined by opening and closing the cut off valve.

Microprocessor 26 of FIG. 9 includes an external non-volatile read/write memory subsystem, peripheral devices to support this memory system, reset circuit, a clock oscillator, a data acquisition subsystem and a visual annunciator subsystem. The discrete components are conventional parts which have input and output pins configured in a conventional manner with the connections being made in accordance with instructions provided by the device manufacturers. The microprocessor used in connection with the device of the invention is designed and programmed specifically so as to provide controlled and repeatable amounts of aerosol to a patient upon actuation. The microprocessor must have sufficient capacity to make calculations in real time. Adjustments can be made in the program so that when the patient's inspiratory flow profile is changed such is taken into consideration. This can be done by allowing the patient to inhale through the device as a test (monitoring event) in order to measure air flow with preferred delivery points determined based on the results of several inhalations by each particular patient. This process can be readily repeated when the inspiratory flow profile is changed for whatever reason. When the patient's lung function has decreased the program will automatically back down in terms of the threshold levels required for release of aerosol. This "back down" function insures delivery to a patient in need but with impaired lung function. Determination of optimal delivery points in the inspiratory flow can be done at each dosing event, daily, weekly, or with the replacement of a new cellular array in the device.

The microprocessor 26 of the present invention, along with its associated peripheral devices, can be programmed so as to prevent triggering the actuation mechanism 28 more than a given number of times within a given period of time. This feature makes it possible to prevent overdosing the patient. The overdose prevention feature can be particularly designed with each individual patient in mind or designed with particular groups of patients in mind. For example, the microprocessor can be programmed so as to prevent the release of more than approximately 200 $\mu$g of a given respiratory drug per day when the patient is normally dosed with approximately 100 $\mu$g of drug per day. The device can be designed to switch off this lock-out function so that drug can be delivered in an emergency situation.

The systems can also be designed so that only a given amount of a particular formulation such as a respiratory drug is provided at a given dosing event. For example, the system can be designed so that only approximately 10 $\mu$g of respiratory drug is given in a given 15-minute period over which the patient will make approximately 10 inhalations with 1 $\mu$g of drug being delivered with each inhalation. By providing this feature, greater assurances are obtained with respect to delivering the respiratory drug gradually over time and thereby providing relief from the symptoms of respiratory disease without overdosing the patient.

The microprocessor 26 of the invention can be connected to external devices permitting external information to be transferred into the microprocessor of the invention and stored within the non-volatile read/write memory available to the microprocessor. The microprocessor of the invention can then change its drug delivery behavior based on this information transferred from external devices. All of the features of the invention are provided in a portable, programmable, battery-powered, hand-held device for patient use which has a size which compares favorably with existing metered dose inhaler devices.

The microprocessor 26 of the present invention is programmed so as to allow for monitoring and recording data from the inspiratory flow monitor without delivering drug. This is done in order to characterize the patient's inspiratory flow profile in a given number of monitoring events, which monitoring events preferably occur prior to dosing events. After carrying out a monitoring event, the preferred point within the inspiratory cycle for aerosol delivery can be calculated. This calculated point is a function of measured inspiratory flow rate as well as calculated cumulative inspiratory flow volume. This information is stored and used to allow activation of the electronic actuation means when the inhalation cycle is repeated during the dosing event.

The amount of aerosol delivered to the patient will vary greatly depending on the particular compound being delivered. In accordance with the present invention it is possible to deliver a wide range of different systemic effect and local effect drugs. For local effect some preferred drugs are albuterol, beclomethasone dipropionate, triamcinolone acetonide, flunisolide, cromolyn sodium, and ipratropium bromide, and include, free acids, bases, salts and various hydrate forms thereof generally administered to a patient in an amount in the range of about 100 $\mu$g–10,000 $\mu$g. These doses are based on the assumption that when intrapulmonary delivery methodology is used the efficiency of the delivery is approximately 10% and adjustments in the amount released must be made in order to take into account the efficiency of the device. The differential between the amount of aerosol actually released from the device and the amount of respiratory drug actually delivered to the patient varies due to a number of factors. The efficiency of the delivery will vary somewhat from patient to patient and must be taken into account when programming the device.

When administering drug using the inhalation device of the present invention, the entire dosing event can involve the administration of anywhere from 10 $\mu$l to 1,000 $\mu$l, but more preferably involves the administration of approximately 100 $\mu$l to 10,000 $\mu$l of formulation. Very small amounts of drug (e.g., nanogram amounts) may be dissolved or dispersed within a pharmaceutically acceptable, liquid, excipient material to provide a liquid, flowable formulation which can be readily aerosolized. The container will include the formulation having drug therein in an amount of about 10 $\mu$g to 300 $\mu$g, more preferably about 50 $\mu$g. The large variation in the amounts which might be delivered are due to different drug potencies and different delivery efficiencies for different devices, formulations and patients. The entire dosing event may involve several inhalations by the patient with each of the inhalations being provided with drug from the device. For example, the device can be programmed so as to release the contents of a single container or to move from one container to the next on a package of interconnected containers. Delivering smaller amounts from several containers can have advantages. Since only small amounts are delivered from each container and with each inhalation, even a complete failure to deliver drug with a given inhalation is not of great significance and will not seriously disturb the reproducibility of the dosing event. Further, since relatively small amounts are delivered with each inhalation, the patient can safely administer a few additional micrograms of drug (or milligrams for some drugs) without fear of overdosing.

In addition to (1) the target area of the lung, (2) drug potency, (3) delivery efficiency, and (4) drug sensitivity must be taken into consideration. The present invention makes it possible to vary dosing over time if sensitivity changes and/or if user compliance and/or lung efficiency changes over time.

Based on the above, it will be understood that the dosing or amount of drug (and in particular volume of aerosolized respiratory drug) actually released from the device can be changed based on the most immediately prior monitoring event wherein the inspiratory flow of a patient's inhalation is measured.

Variations in doses are calculated by monitoring the effect of one or more lung function parameters in response to known amounts of respiratory drug released from each container and delivered to the patient. If the response in changing measured lung function parameters is greater than with previous readings, then the dosage (number of containers released) is decreased or the minimum dosing interval is increased. If the response in changing measured lung function parameters is less than with previous readings, then the dosing amount is increased or the minimum dosing interval is decreased. The increases and decreases are gradual and are preferably based on averages (of 10 or more readings of lung function parameter after 10 or more dosing events) and not a single dosing event and monitoring event. The preferred drug delivery device of the present invention can record dosing events and lung function parameters over time, calculate averages and deduce preferred changes in administration of respiratory drug.

One of the important features and advantages of the present invention is that the microprocessor can be programmed to take two different criteria into consideration with respect to dosing times.

Specifically, the microprocessor can be programmed so as to include a minimum time interval between doses i.e. after a given delivery another dose cannot be delivered until a given period of time has passed. Secondly, the timing of the device can be programmed so that it is not possible to exceed the administration of a set maximum amount of drug within a given time. For example, the device could be programmed to prevent dispersing more than 200 mg of a particular respiratory drug within one hour. More importantly, the device can be programmed to take both criteria into consideration. Thus, the device can be programmed to include a minimum time interval between doses and a maximum amount of drug to be released within a given time period. For example, the microprocessor could be programmed to allow the release of a maximum of 200 mg of a given respiratory drug during an hour which could only be released in amounts of 25 mg with each release being separated by a minimum of five minutes.

The dosing program can be designed with some flexibility. For example, if the patient normally requires 250 $\mu$g per day of respiratory drug, the microprocessor of the inhalation device can be programmed to provide a warning after 250 $\mu$g have been administered within a given day and to continue the warning thereafter to alert the user of possible overdoses. By providing a warning and not a lock-out, the device allows for the patient to administer additional drug, if needed, due to a decreased lung function and/or account for misdelivery of drug such as due to coughing or sneezing during an attempted delivery.

The ability to prevent overdosing is a characteristic of the device due to the ability of the device to monitor the amount of drug released and calculate the approximate amount of drug delivered to the patient based on monitoring a variety of lung function parameters. The ability of the present device to prevent overdosing is not merely a monitoring system which prevents further manual actuation of a button. As indicated above, the device used in connection with the present invention is not manually actuated, but is fired in response to an electrical signal received from a microprocessor (which received data from a monitoring device such as a device which monitors inspiratory flow) and allows the actuation of the device upon achieving an optimal point in a inspiratory cycle. When using the present invention, each release of the valve is a release which will administer drug to the patient in that the valve is released in response to patient inhalation. More specifically, the device does not allow for the release of respiratory drug merely by the manual actuation of a button to fire a burst of respiratory drug into the air or a container.

The microprocessor 26 of the present invention preferably includes a timing device. The timing device can be electrically connected with visual display signals as well as audio alarm signals. Using the timing device, the microprocessor can be programmed so as to allow for a visual or audio signal to be sent when the patient would be normally expected to administer drug. In addition to indicating the time of administration (preferably by audio signal), the device can indicate the amount of respiratory drug which should be administered by providing a visual display. For example, the audio alarm could sound alerting the patient that drug should be administered. At the same time, the visual display could indicate "one dosage unit" as the amount of drug (number of containers) to be administered. At this point, a monitoring event could take place. After completion of the monitoring event, administration would proceed and the visual display would continually indicate the remaining amount of drug which should be administered. After the predetermined dose (e.g., indicated number of containers) had been administered, the visual display would indicate that the dosing event had ended. If the patient did not complete the dosing event by administering the stated amount of drug, the patient would be reminded of such by the initiation of another audio signal, followed by a visual display instructing the patient to continue administration.

Additional information regarding dosing with drugs can be found within Harrison's—Principles of Internal Medicine (most recent edition) and the Drug Evaluation Manual, 1993 (AMA—Division of Drugs and Toxicology), both of which are published by McGraw Hill Book Company, New York, and the 1997 edition of the Physicians Desk Reference incorporated herein by reference to disclose conventional information regarding drugs in general, the dosing of drugs and in particular respiratory drugs as well as other useful drugs and diagnostic formulations which can be aerosolized and delivered per the present invention.

After drug has been delivered it is possible to discontinue any readings with respect to flow and/or volume. However, it is preferable to continue readings with respect to both criteria after drug has been released. By continuing the readings the adequacy of this patient's particular drug delivery maneuver can be determined. All of the events are recorded by the microprocessor. The recorded information can be provided to the care giver for analysis. For example, the care giver can determine if the patient correctly carried out the inhalation maneuver in order to correctly deliver drug and can determine if the patient's inhalation profile is effected by the drug (e.g. with respiratory drugs) in order to determine the effectiveness of the drug in treating the patient's particular condition. If necessary, various adjustments can be made, such as in the type of drug or the particle size to obtain a particular desired result.

The instant invention is shown and described herein in the most practical and preferred embodiments. It is recognized, however, that departures therefrom and obvious modifications that are within the scope of the invention will occur to one skilled in the art upon reading this disclosure. Therefore, it is to be understood that this invention is not limited to the particular methodology, devices, containers and formulations described, which may, of course, vary. It is also to be understood that the terminology used herein is for the purpose of describing particular embodiments only, and is not intended to limit the scope of the present invention, which will be limited only by the appended claims.

What is claimed is:

1. A device for delivering an aerosolized drug formulation for inhalation by a patient, the device comprising a plurality of containers having therein a drug formulation, each container having a cover;

a means for holding a first container in a drug release position;

a means for extruding the drug formulation from the first container into a channel, wherein the patient inhales the formulation from the channel; the means comprising a cam assembly, the cam assembly comprising a first cam shaft mechanically connected to a power source, and an extrusion cam, the extrusion cam connected to the first cam shaft, wherein the extrusion cam exerts pressure on a first container whereby the drug formulation is extruded from the first container;

a clamping cam, wherein the clamping cam forces a clamping member against the cover of the first container; and, an advancement cam, wherein the advancement cam advances each of the plurality of containers into drug release position for extruding the drug formulation for inhalation by the patient.

2. The device of claim 1, wherein the extrusion cam, clamping cam, and advancement cam are connected to the first cam shaft.

3. The device of claim 1, wherein the power source is an electric motor.

4. The device of claim 1, wherein the clamping cam is connected to the first cam shaft.

5. The device of claim 1, wherein said advancement cam is connected to the first cam shaft and is fitted with a component for engaging and moving a container of drug formulation.

6. The device of claim 3, further comprising:

a battery connected to the electric motor.

7. The device of claim 6, wherein the container is comprised of a collapsible wall and porous membrane.

8. The device of claim 1 wherein the drug formulation is a substantially dry drug formulation.

9. The device of claim 1, further comprising:

a mouthpiece at the open end of the channel.

10. The device of claim 9, wherein the device is a hand held, self-contained inhaler device.

11. The device of claim 1, further comprising:

a signal means for prompting a patient to inhale at a preferred rate.

12. The device of claim 1, further comprising:

an air flow sensor.

13. The device of claim 1, further comprising:

an actuation means for delivering a controlled amount of formulation to a specific volume of air.

* * * * *